United States Patent
Onishi et al.

(10) Patent No.: US 9,322,711 B2
(45) Date of Patent: Apr. 26, 2016

(54) LIGHT SIGNAL DETECTING CIRCUIT, LIGHT AMOUNT DETECTING DEVICE, AND CHARGED PARTICLE BEAM DEVICE

(71) Applicant: HITACHI HIGH-TECHNOLOGIES CORPORATION, Tokyo (JP)

(72) Inventors: Fujio Onishi, Tokyo (JP); Hiroshi Touda, Tokyo (JP); Tetsuji Osawa, Tokyo (JP); Yuki Sugawara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/407,768

(22) PCT Filed: Jun. 14, 2013

(86) PCT No.: PCT/JP2013/066502
§ 371 (c)(1),
(2) Date: Dec. 12, 2014

(87) PCT Pub. No.: WO2013/187511
PCT Pub. Date: Dec. 19, 2013

(65) Prior Publication Data
US 2015/0153223 A1 Jun. 4, 2015

(30) Foreign Application Priority Data

Jun. 15, 2012 (JP) ................................. 2012-135770

(51) Int. Cl.
*H01J 37/24* (2006.01)
*G01J 1/44* (2006.01)
(Continued)

(52) U.S. Cl.
CPC .... *G01J 1/44* (2013.01); *G01J 1/42* (2013.01); *G01N 23/2251* (2013.01);
(Continued)

(58) Field of Classification Search
CPC ......... H03F 3/08; G01N 23/2551; G01J 1/42; H01J 37/244
See application file for complete search history.

(56) References Cited

U.S. PATENT DOCUMENTS

| 4,602,282 | A | 7/1986 | Kurono et al. |
| 7,157,681 | B1 * | 1/2007 | Tetzlaff ................... H01J 43/04 250/205 |

(Continued)

FOREIGN PATENT DOCUMENTS

| JP | 59-004286 A | 1/1984 |
| JP | 2006-300728 A | 11/2006 |
| WO | 2012/017762 A1 | 2/2012 |

*Primary Examiner* — Tony Ko
(74) *Attorney, Agent, or Firm* — Mattingly & Malur, PC

(57) ABSTRACT

A light signal detecting circuit, a light amount detecting device, and a charged-particle-beam device capable of discriminating the signal component of a small amount of light from the signal component of noise due to dark current. A data-processing-unit detects pulses from digital voltage signal corresponding to an amount of light obtained by an amplifier and an A-D converter, calculates a crest value as the maximum voltage value of each pulse, and stores the occurrence frequency of each calculated crest value in a frequency occurrence storage area. A data analysis unit compares a previously-determined frequency lower limit with the occurrence frequency of each crest value in ascending order of the crest values and sets a pulse determination threshold to the first crest value whose occurrence frequency is equal to or smaller than the frequency lower limit. The threshold processing unit thus outputs the digital signal higher than the pulse determination threshold.

7 Claims, 17 Drawing Sheets

(51) Int. Cl.
*G01J 1/42* (2006.01)
*H01J 37/244* (2006.01)
*G01N 23/225* (2006.01)
*H03F 3/08* (2006.01)
*G01N 21/64* (2006.01)

(52) U.S. Cl.
CPC ............... *H01J 37/244* (2013.01); *H03F 3/08* (2013.01); *G01N 21/64* (2013.01); *H01J 2237/2443* (2013.01); *H01J 2237/2445* (2013.01); *H01J 2237/24495* (2013.01); *H03F 2201/3215* (2013.01)

(56) References Cited

U.S. PATENT DOCUMENTS

| | | | |
|---|---|---|---|
| 7,710,557 B2 * | 5/2010 | Oshima | G01N 21/9501 250/559.45 |
| 8,624,192 B2 * | 1/2014 | Normand | H01J 43/04 250/214 AG |
| 2013/0114073 A1 | 5/2013 | Namba et al. | |

\* cited by examiner

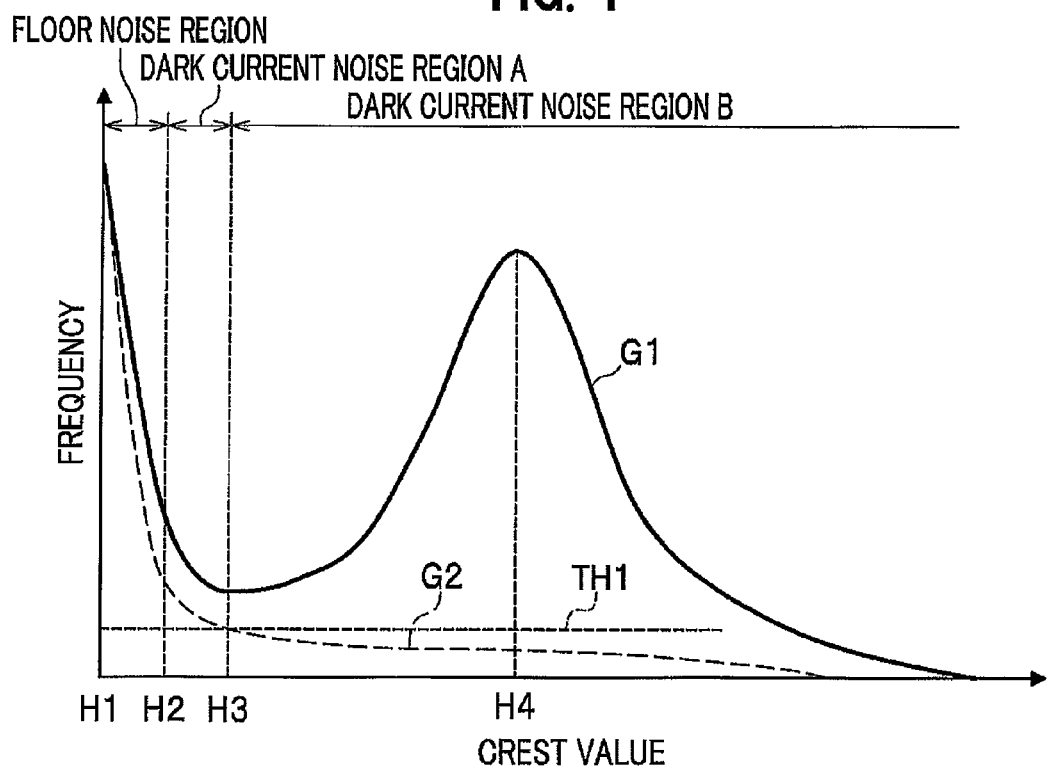
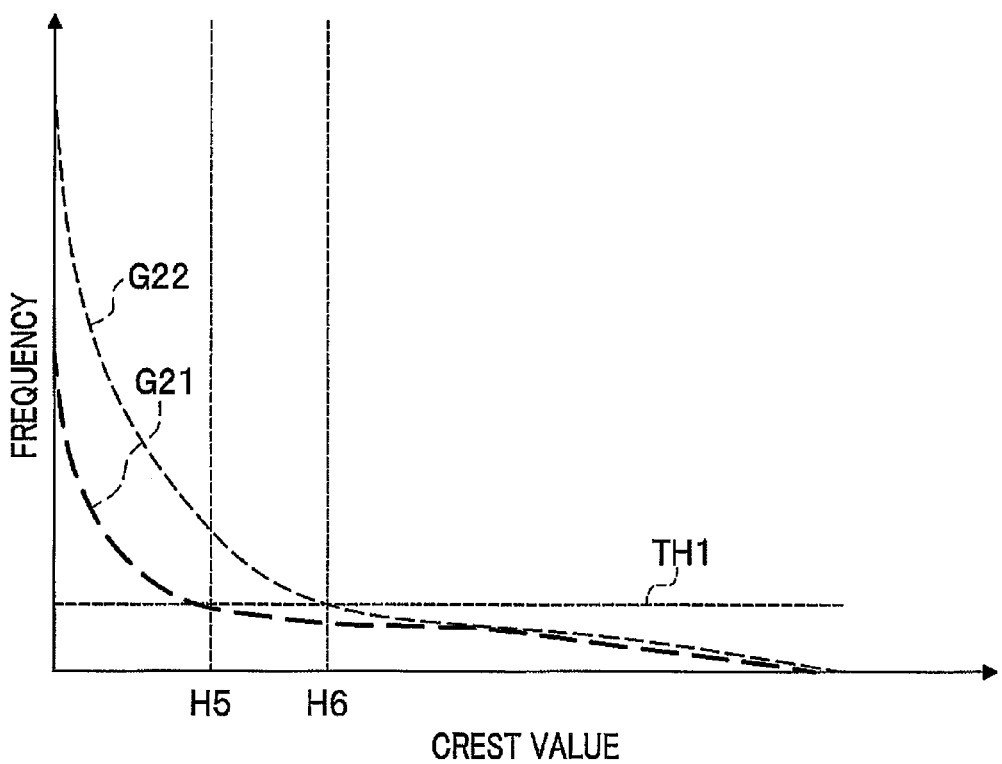

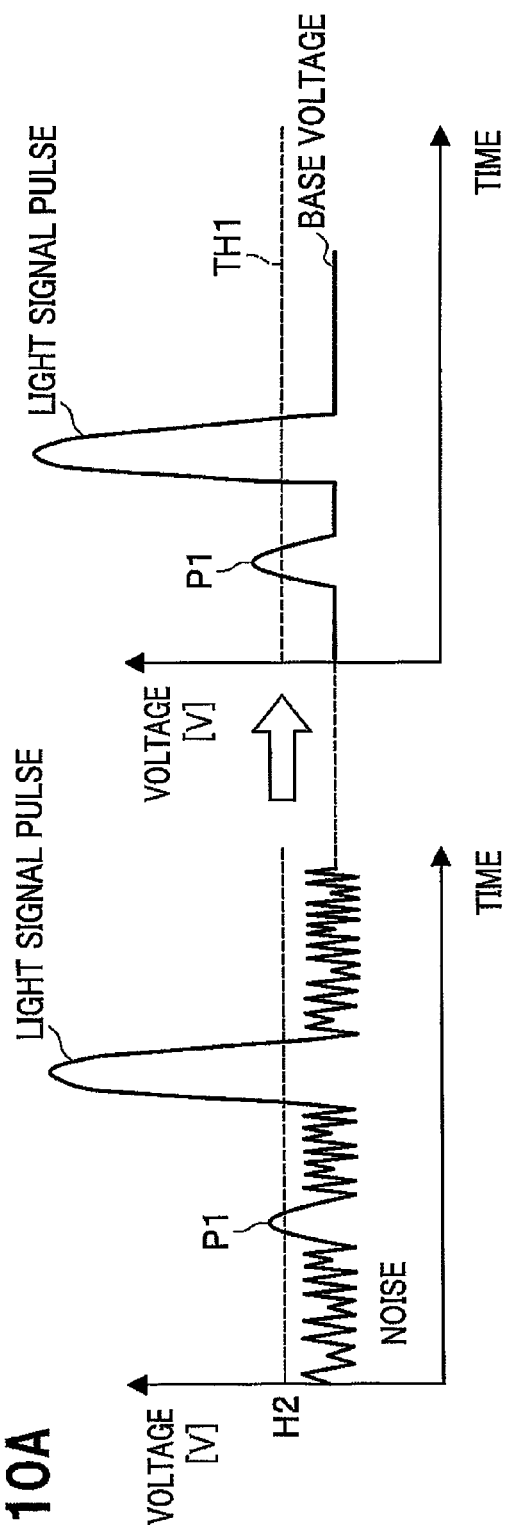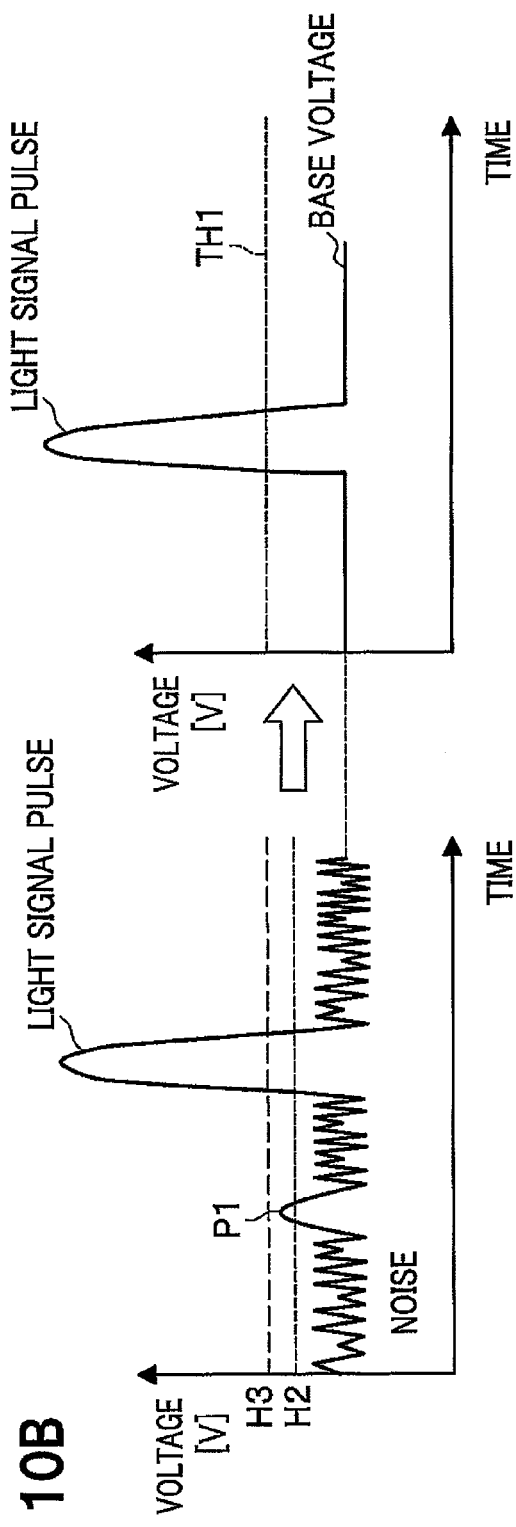
FIG. 10A
FIG. 10B

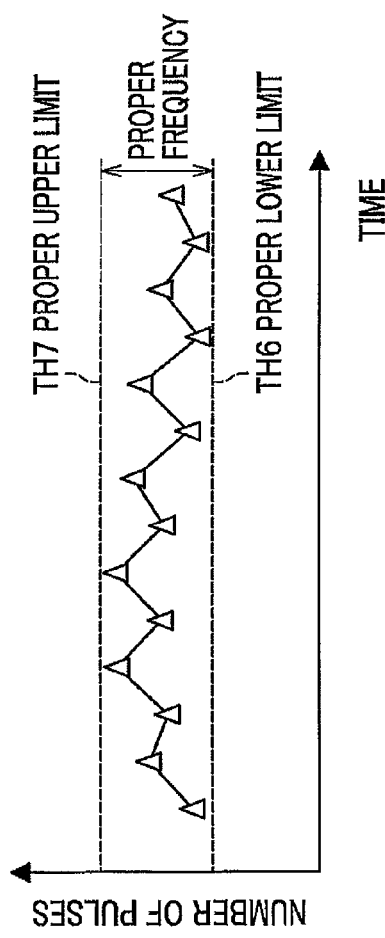
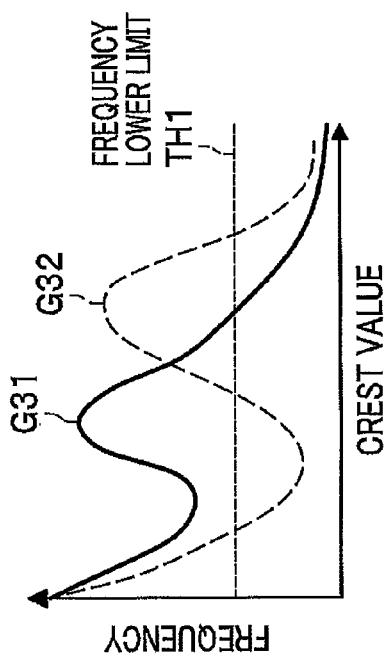
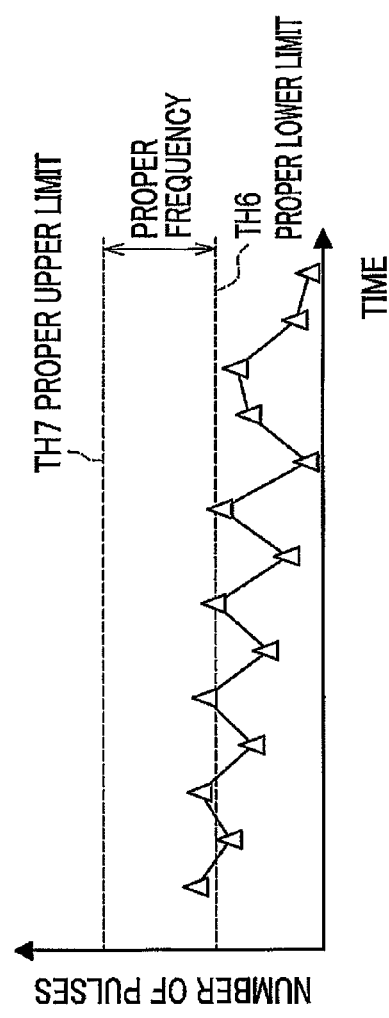
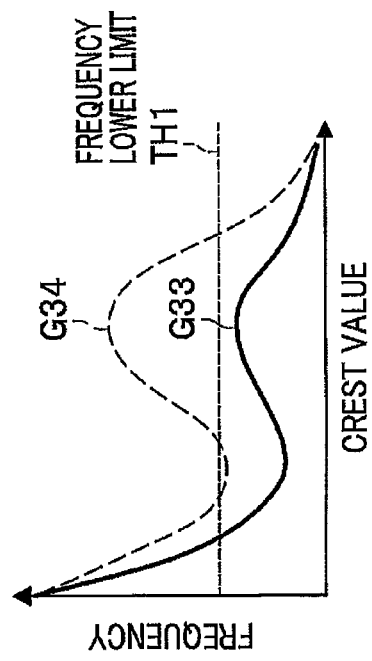

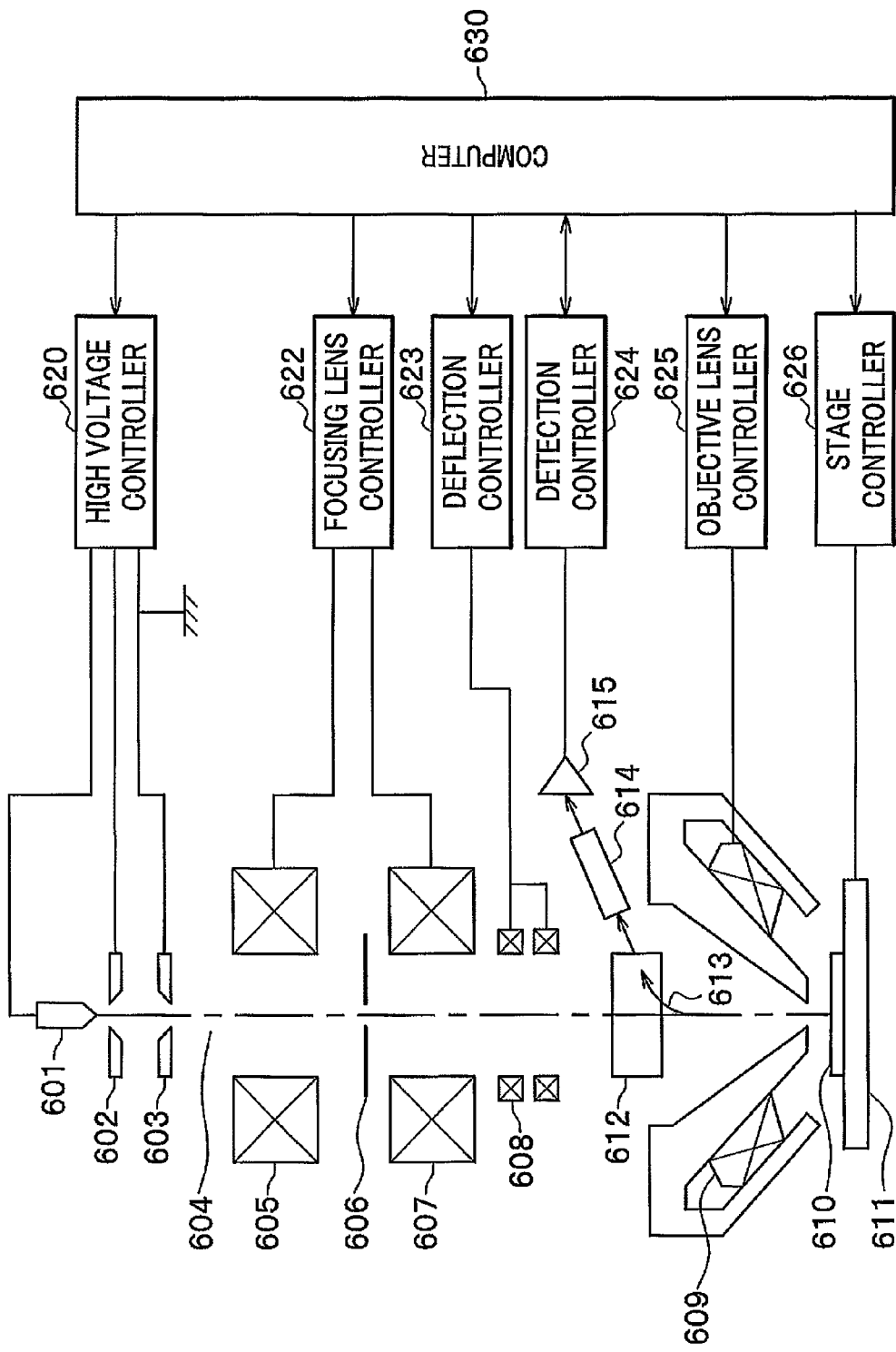

LIGHT SIGNAL DETECTING CIRCUIT, LIGHT AMOUNT DETECTING DEVICE, AND CHARGED PARTICLE BEAM DEVICE

TECHNICAL FIELD

The present invention relates to a light signal detecting circuit, a light amount detecting device, and a charged particle beam device, which detect light emitted from samples.

BACKGROUND ART

Photomultiplier tubes are capable of extracting very faint light as electric signal and are therefore used in various kinds of fields. For example, a photometer analyses the components contained in a small amount of a sample by projecting light onto the sample and detecting fluorescence emitted from the sample through the transmitted light, scattering light, or the like with a photomultiplier tube. A charged particle beam device or the like projects an electron beam onto a sample and detects a small amount of secondary electrons generated from the surface of the sample using a scintillator and a photomultiplier tube in combination, thus enabling a detailed observation of the surface of the sample.

However, in recent years, photometers are required to analyze the components contained in extremely small amounts of samples, and charged particle beam devices are required to enable more detailed and clearer observation of sample surfaces. Accordingly, it is necessary to detect electric signals from photomultiplier tubes produced by very small amounts of light.

One of the techniques to detect electric signals from a photomultiplier tube which is produced by a very small amount of light is described in Patent Document 1, for example. In the conventional technique described in Patent Document 1, a light detecting circuit is connected to an anode of the PMT (photomultiplier tube). The light detecting circuit includes: an I/V converter converting current outputted from the anode into voltage signal V1: a dark current removing circuit removing dark current (dark count) from voltage signal V1 to generate voltage signal V2; a primary delay filter circuit shaping the voltage signal V2; an A-D converter converting voltage signal V3 having passed through the primary delay filter circuit into digital data; and an arithmetic processing unit (CPU) integrating the digital data to create light amount data corresponding to the amount of light that enters the PMT. The CPU increases the integration time as the value of the digital data decreases.

PRIOR ART DOCUMENTS

Patent Document

Patent Document 1: Japanese Patent Laid-open Publication No. 2006-300728

SUMMARY OF THE INVENTION

Problems to be Solved by the Invention

In order to detect electric signal produced from a small amount of light by a photomultiplier tube, it is necessary to discriminate the signal component of light from the signal component of noise and remove the signal component of noise. The conventional technique of Patent Document 1 describes removing noise due to dark current by off-set adjustment of an amplifying circuit included in the dark current removing circuit. However, Patent Document 1 does not describe any specific method of the off-set adjustment.

The characteristic of noise due to dark current depends on temperature. In the conventional technique described in Patent Document 1, the measurer needs to perform the offset adjustment of the amplifier at each time in response to changes in temperature. Generally, the offset adjustment of the amplifying circuit handling analogue signals needs finer control than that in the case of handling digital signals, thus requiring time and effort.

The present invention has been made in the light of the aforementioned problems, and an object of the present invention is to provide a light signal detecting circuit, a light amount detecting device, and a charged particle beam device which are capable of discriminating the signal component of a small amount of light from the signal component of noise due to dark current with a simple operation.

Means for Solving the Problems

A light signal detecting circuit according to the present invention includes: an amplifier for amplifying an analogue detection signal corresponding to an amount of light detected by a light detecting means; an analogue-to-digital converting means for converting the analogue detection signal amplified by the amplifier to a digital detection signal; a threshold determination means configured to: repeat a process to detect a pulse from the digital detection signal obtained by the analogue-to-digital converting means and detect energy of the detected pulse; calculate an occurrence frequency of the pulses of each value of the energy; and determine a pulse determination threshold based on the calculated occurrence frequency of the pulses of each value of the energy; and a threshold processing means for outputting, as a detection signal, the digital detection signal including the pulses of the values of the energy not lower than the pulse determination threshold determined by the threshold determination means.

Effects of the Invention

According to the present invention, it is possible to provide a light signal detecting circuit, a light amount detecting device, and a charged particle beam device which are capable of discriminating the signal component of a small amount of light from the signal component of noise due to dark current with a simple operation.

BRIEF DESCRIPTION OF THE DRAWINGS

FIG. 1 is a diagram illustrating a pulse crest distribution of output pulses from a photomultiplier tube which receives a small amount of light from a sample irradiated by a light source and noise pulses.

FIG. 2 is a diagram illustrating a change in the pulse crest distribution of noise pulses with temperature.

FIG. 8A is a diagram for explaining the time, voltage, and on/off of a pulse duration flag, and FIG. 8B is a diagram for explaining addresses (crest values) and data (number of occurrences) stored in a frequency count storage area.

FIGS. 10A and 10B are diagrams illustrating outputs from the light signal detecting circuit of Embodiment 1, where FIG. 10A is a diagram illustrating a light signal pulse outputted and a pulse P1 due to dark current noise where a frequency lower limit TH1 is set to a frequency at a crest value H2 as a boundary between a floor noise region and a dark current noise region A (illustrated in FIG. 1), and FIG. 10B is a diagram illustrating a light signal pulse outputted where the frequency lower limit TH1 is set to a crest value H3 as the boundary between the dark current noise region A and a dark current region B (illustrated in FIG. 1).

FIGS. 13A to 13D are diagrams for explaining the conditions for gain adjustment, where FIG. 13A is a diagram illustrating the relation between crest values and frequency after a predetermined period of time from the start of measurement, the drawing showing that when the frequency of the crest value serving as a pulse determination threshold is larger than the frequency lower limit TH1 (line G31), it is preferable that the frequency of the crest value serving as the pulse determination threshold is adjusted to be lower than the frequency lower limit TH1 (line G32), FIG. 13B is a diagram illustrating the number of pulses detected for each unit time in the case of FIG. 13A, FIG. 13C is a diagram illustrating the relation between crest values and frequency after a predetermined period of time from the start of measurement, the drawing showing that when the frequency of the crest value serving as the pulse determination threshold is lower than the frequency lower limit TH1 and the frequency of crest values distributed around the crest value determined by the multiplying characteristic of the photomultiplier tube is also lower than the frequency lower limit TH1 (line G33), it is preferable that the frequency of crest values distributed around the crest value determined by the multiplying characteristic of the photomultiplier tube is also set higher than the frequency lower limit TH1 (line G34), and FIG. 13D is a diagram illustrating the number of pulses for each unit time in the case of FIG. 13C.

FIG. 18 is a diagram illustrating the configuration of a scanning electron microscope including the light signal detecting circuit of the present invention.

MODES FOR CARRYING OUT THE INVENTION

Figure 3:
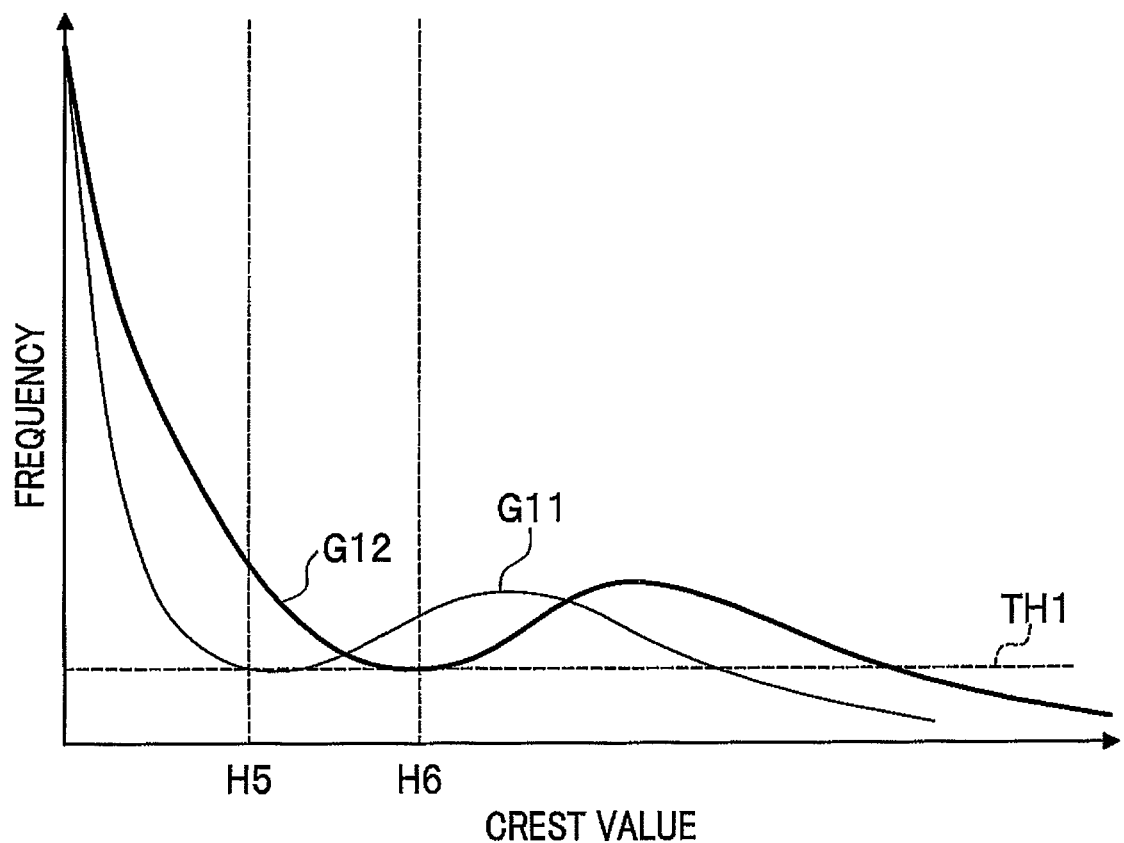
FIG. 3 is a diagram illustrating the case where the pulse crest distribution of the output from the photomultiplier tube changes because of an increase in the voltage of high-voltage power supply of the photomultiplier tube with a change in the surrounding environment.

Hereinafter, embodiments of the present invention are described in detail with reference to the drawings. In the description of the embodiments, a crest value as the maximum voltage value of each detected pulse is taken as an example of energy. However, the energy is not limited to the crest values.

(Summary and Characteristics)

Summary and characteristics of a light signal detecting circuit according to the present invention are described using FIGS. 1 to 4. FIG. 1 is a diagram illustrating a pulse crest distribution of output pulses from a photomultiplier tube and a pulse crest distribution of noise pulses when a small amount of light from a sample irradiated by a light source goes into the photomultiplier tube. In FIG. 1, the horizontal axis represents crest values, which are maximum voltage values of pulses, and the vertical axis represents the occurrence frequency (the number of occurrences) of each crest value in a measurement time. As represented by a dashed line G2 of FIG. 1, the occurrences of noise pulse crest values are concentrated on low crest values, and the occurrence frequency thereof rapidly lowers between crest values H1 and H2. The occurrence frequency of noise pulse crest values lowers more slowly between the crest value H2 and a crest value H3 than between the crest values H1 and H2. Moreover, the occurrence frequency of noise pulse crest values lowers in a region larger than the crest value H3 still more slowly than between the crest values H2 and H3.

As for the crest values of output pulses from the photomultiplier tube, as represented by the line G1 of FIG. 1, the occurrence frequency of the crest values of output pulses rapidly lowers between the crest values H1 and H3 under the influence of the noise pulses. For crest values larger than the crest value H3, the occurrences of the output pulse crest values are distributed around a crest value H4, which is determined by the multiplying characteristic of the photomultiplier tube.

Herein, the attention is focused on the characteristics of noise pulses of FIG. 1. Since the electric output from a photomultiplier tube is very small, crest values of output pulses from the photomultiplier tube are generally measured in such manner that the output from the photomultiplier tube is amplified with a pre-amplifier and the amplified signal is converted to digital signal using an A-D converter. Accordingly, the noise pulses include noise pulses due to dark current produced when no light goes into the photomultiplier tube (dark current noise pulses) and noise pulses due to floor noise caused by the pre-amplifier and the like when the photomultiplier tube is not operating (floor noise pulses).

The floor noise includes waveforms having various frequency characteristics. Generally, the amplitude of floor noise is smaller than the average crest value of noise due to dark current. Accordingly, in a region between the crest values H1 and H2 in FIG. 1 (a floor noise region), the floor noise has a larger influence than the noise due to dark current. Between the crest values H2 and H3 (a dark current noise region A), the floor noise has very little influence while the noise due to dark current has a large influence. This is because the crest values of dark current noise pulses are equal to the crest values of original output pulses from photomultiplier tube due to light. In a region of crest values larger than the crest value H3 (a dark-current noise region B), the noise due to dark current has very little influence because the crest values of output pulses from the photomultiplier tube are larger than the crest values of dark current noise pulses. The output pulses from the photomultiplier tube are distributed around the crest value H4, which is determined by the multiplying characteristic of the photomultiplier tube. Accordingly, it is desirable that only the crest values in the dark current noise region B are detected for light signal detection.

As described using FIG. 1 above, the output pulses from the photomultiplier tube are distributed around the crest value H4, which is determined by the multiplying characteristics of the multiplier tube. Accordingly, with respect to low to high output pulse crest values, the occurrence frequency thereof rapidly lowers up to the boundary between the dark current noise region A, in which the dark current noise has a large influence, and the dark current noise region B and gradually increases from the boundary.

In the embodiments, the pulse determination threshold used to detect pulses is determined by focusing attention on the fact that with respect to low to high crest values, the occurrence frequency thereof rapidly lowers to the boundary between the dark current-noise region A, in which the dark current noise has a large influence, and the dark current-noise region B and gradually increases from the boundary. Specifically, at the start of light measurement, the frequency counts corresponding to respective crest values are stored, and the crest value whose occurrence frequency is equal to or lower than a previously set frequency lower limit TH1 is determined as the pulse determination threshold. (Only) the pulses having crest values larger than the pulse determination threshold are detected and outputted as the pulses.

The characteristic of noise pulses changes depending on temperature. FIG. 2 is a diagram illustrating a change in the pulse crest distribution of noise pulses depending on temperature. In FIG. 2, the horizontal axis represents the crest values, and the vertical axis represents the occurrence frequency of each crest value in the measurement time. In FIG. 2, a line G21 represents the characteristic of noise pulses at the start of light amount detection. A line G22 represents the characteristic of noise pulses when the temperature of the photomultiplier tube or the voltage of the high-voltage power supply is higher than that at the start of light amount detection after a certain time from the start of light amount detection. As illustrated in FIG. 2, when the temperature of the photomultiplier tube or the voltage of the high-voltage power supply increases, the occurrence frequency counts of the crest values of dark current noise pulses become higher than those with lower temperature or lower voltage of the high-voltage power supply. To be specific, the crest values whose occurrence frequency is not higher than the frequency lower limit TH1 are not smaller than a crest value H5 in the line G21, which represents the characteristic of noise pulses with low temperature or low voltage of the high-voltage power supply, and are not smaller than a crest value H6 (H5<H6) in a line G22, which represent the characteristic thereof with high temperature or high voltage of the high-voltage power supply. Accordingly, it is desirable that crest values not smaller than the crest value H6 are detected as light signal when the characteristic of noise pulses changes from the line G21 to the line G22 with an increase in temperature or voltage of the high-voltage power supply.

When the temperature or the voltage of the high-voltage power supply becomes lower than that at the start of measurement, it is desirable to detect light signal in the following manner. When the characteristic of noise pulses changes from the line G22 in FIG. 2 to the line G21 because the temperature or the voltage of the high-voltage power supply is lowered, the crest value H6 is used as the pulse determination threshold at the start of measurement to detect pulses whose crest values are equal to or larger than the crest value H6 as the light signal. After the characteristic of noise pulses changes to the line G21, the crest value H5 is used as the pulse determination threshold to detect pulses whose crest values are equal to or larger than the crest value H5 as the light signal.

FIG. 3 is a diagram illustrating the case where the pulse crest distribution of the outputs from the photomultiplier tube changes when the voltage of the high-voltage power supply of the photomultiplier tube increases with changes in the surrounding environment. In FIG. 3, the horizontal axis represents the crest values, and the vertical axis represents the occurrence frequency of each crest value in the measurement time.

In FIG. 3, a line G11 represents the characteristic of output pulses from the photomultiplier tube under the characteristic of noise pulses at the start of light amount detection which is represented by the line G21 of FIG. 2. A line G12 represents the characteristic of output pulses from the photomultiplier tube under the characteristic of noise pulses at the start of light amount detection which is represented by the line G21 of FIG. 2.

As illustrated in FIG. 3, the line G12 is shifted to the larger crest value side in respect to the line G11 because a certain time has elapsed from the start of light amount detection and the voltage of the high-voltage power supply of the photomultiplier tube becomes higher than that at the start of light detection, for example. To be specific, the boundary between the dark current noise regions A and B illustrated in FIG. 1 above is shifted to the larger crest value side, and the distribution valley corresponding to the boundary between the dark current noise regions A and B is shifted. This shift is caused by the change in the characteristic of noise pulses depending on the voltage of the high-voltage power supply illustrated in FIG. 2. The distribution valley corresponding to the boundary between the dark current noise regions A and B is substantially at the crest value H5 in the line G11, which is attributable to the characteristic of noise pulses represented by the line G21 of FIG. 2, and is substantially at the crest value H6 in the line G12, which is attributable to the characteristic of noise pulses represented by the line G22 of FIG. 2.

Figure 4:
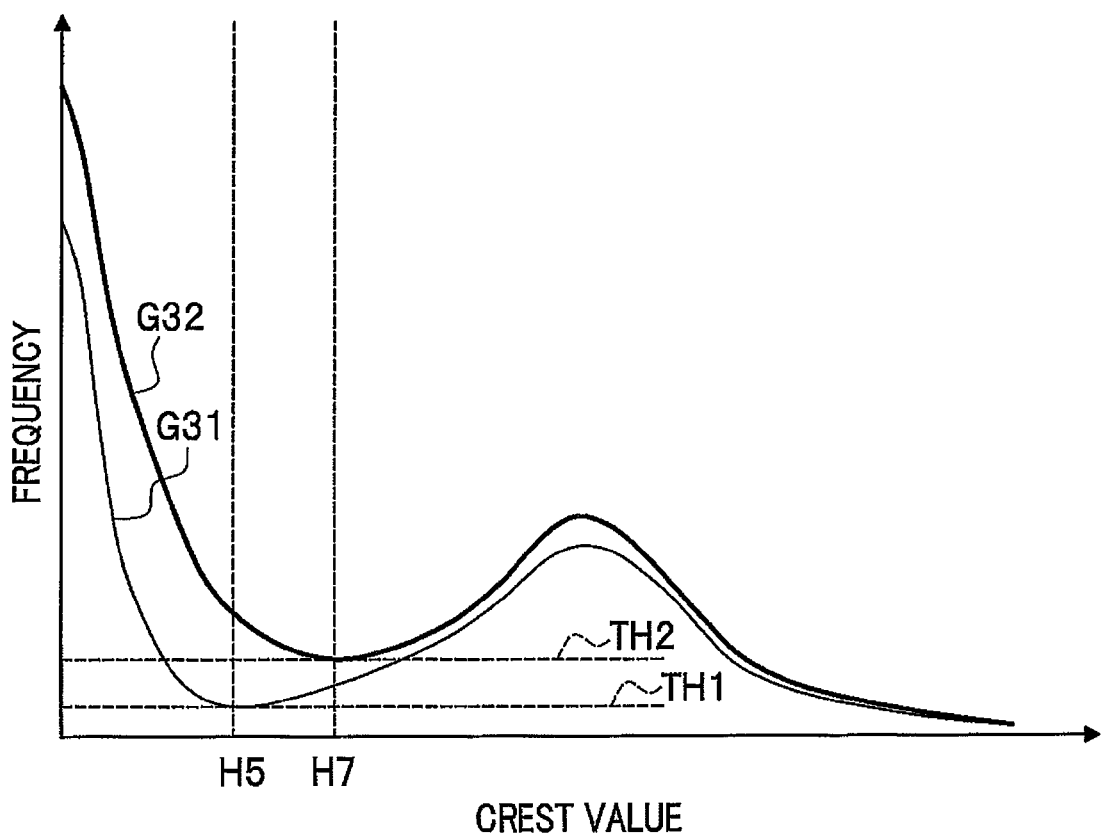
FIG. 4 is a diagram illustrating the case where the pulse crest distribution of the output from the photomultiplier tube changes with an increase in temperature of the photomultiplier tube or with an increase in temperature of the surrounding environment.

FIG. 4 is a diagram illustrating the case where the pulse crest distribution of the output from the photomultiplier tube changes with an increase in temperature of the photomultiplier tube itself or temperature of the surrounding environment. In FIG. 4, the horizontal axis represents the crest values, and the vertical axis represents the occurrence frequency of each crest value in the measurement time.

In FIG. 4, a line G31 represents the characteristic of output pulses from the photomultiplier tube with the characteristic of noise pulses at the start of light amount detection represented by the line G21 of FIG. 2. A line G32 represents the characteristic of output pulses from the photomultiplier tube with the characteristic of noise pulses at the start of light amount detection represented by the line G22 of FIG. 2.

As illustrated in FIG. 4, the line G32 is shifted in such a manner that the frequency of each crest value of noise pulses due to dark current of the line G32 becomes higher than that of the line 31 because a certain time has elapsed from the start of the light amount detection and the temperature of the photomultiplier tube is higher than that at the start of light detection, for example. Specifically, in the dark current noise region A illustrated in FIG. 1 above, the frequency of each crest value is significantly increased. In the dark current noise region B, the frequency of each crest value is increased by a comparatively small amount. The increase in the frequency of each crest value is caused by a change in the characteristic of noise pulses illustrated in FIG. 2 above with an increase in temperature, and the distribution valley corresponding to the boundary between the dark current noise regions A and B is shifted from the crest value H5 to a crest value H7.

Accordingly, in the embodiments, in the light of the fact that with respect to low to high crest values, the occurrence frequency thereof rapidly lowers to the boundary between the dark current noise region A, where dark current noise has a large influence, and the dark current noise region B and gradually increases from the boundary, at the start of light amount measurement, frequency counts associated with crest values are stored, and the crest value whose occurrence frequency is equal to or lower than the previously set frequency lower limit TH1 is set as the pulse determination threshold. Only the pulses larger than the pulse determination threshold are outputted as the detection pulses. The pulse determination threshold is also adjusted during the light measurement by comparing the frequency lower limit TH1 with the occurrence frequency associated with each crest value.

Moreover, in the embodiments, in the light of the fact that with respect to low to high crest values, the occurrence frequency thereof rapidly decreases to the boundary between the dark current noise region A, where dark current noise has a large influence, and the dark current noise region B and gradually increases from the boundary, the detection pulses are outputted in the following manner. During the light measurement, the frequency counts associated with crest values are stored, and the valley of the frequency counts, at which the decreasing frequency count begins to increase, that is, the smallest one of the frequency counts is detected. The crest value whose frequency count is the detected smallest frequency count is set as the pulse determination threshold. The (only) pulses which are larger than the pulse determination threshold are outputted as the detection pulses.

Embodiment 1

Figure 5:
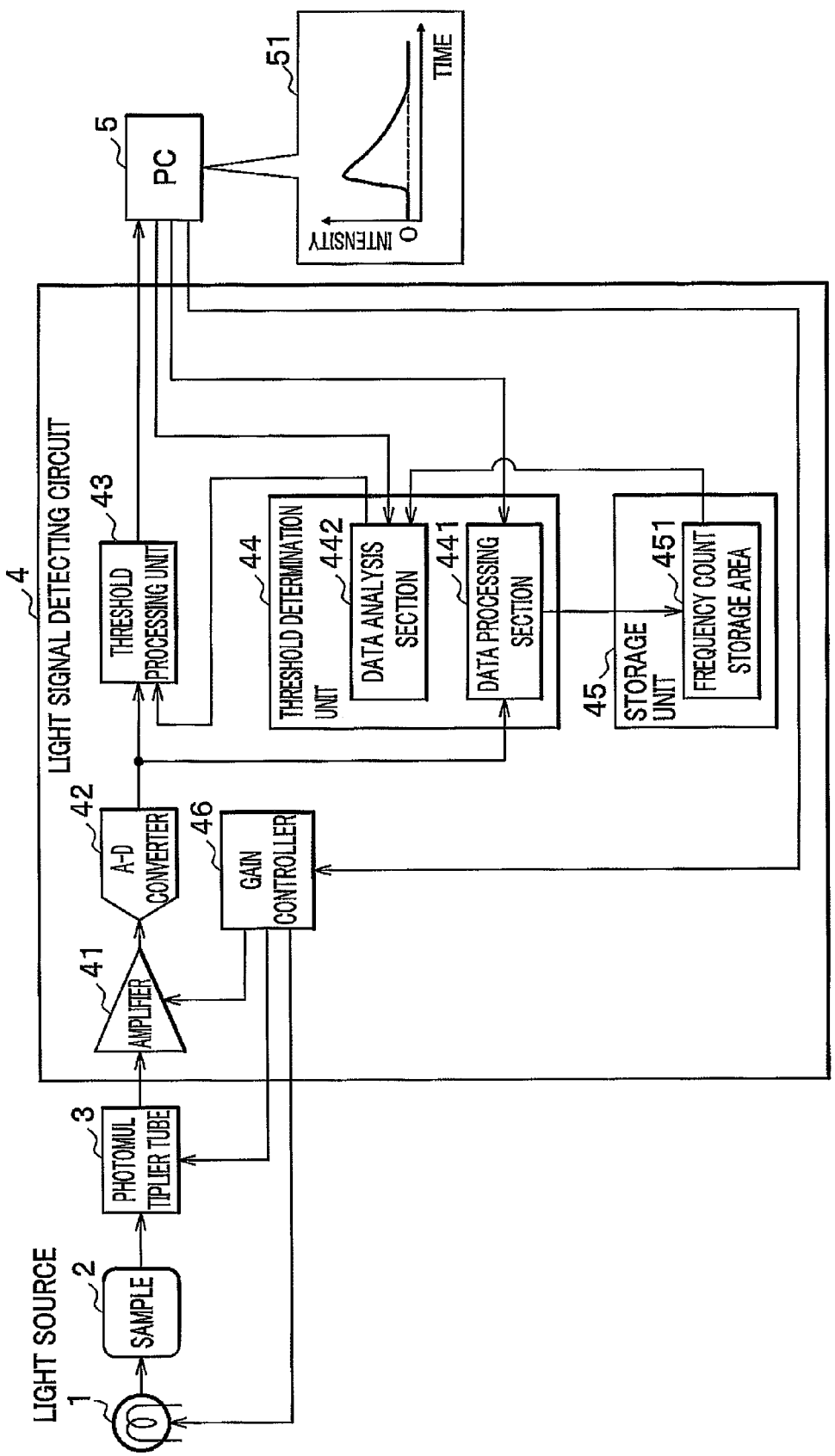
FIG. 5 is a block diagram illustrating the configuration of a light amount detecting device including a light signal detecting circuit of Embodiment 1 of the present invention.

Embodiment 1 of the present invention is described using FIGS. 5 to 9. FIG. 5 is a block diagram illustrating the configuration of a light amount detecting device including a light signal detecting circuit of Embodiment 1 of the present invention. As illustrated in FIG. 5, the light amount detecting device includes a light source 1, a photomultiplier tube 3, a light signal detecting circuit 4, and a personal computer (hereinafter, referred to as a PC) 5 and is configured to detect light from a sample 2. The photomultiplier tube 3 is light detecting means, and a personal computers is controlling means.

The light source 1 projects light onto the sample 2 as a measurement object. The photomultiplier tube 3 detects light transmitted through or reflected on the sample 2 irradiated by the light source 1 with light or fluorescence from the sample 2 generated by irradiation of the sample 2 with light from the light source 1 (these kinds of light are collectively referred to as light from the sample 2). The photomultiplier tube 3 outputs an electric signal corresponding to the light from the sample 2 (hereinafter, referred to as an analogue voltage signal) to the light signal detecting circuit 4. The analogue voltage signal is an analogue detection signal.

The light signal detecting circuit 4 detects an amount of light of the sample 2 from the analogue voltage signal inputted from the photomultiplier tube 3 and outputs the same to the PC 5. The light signal detecting circuit 4 includes an amplifier 41, an analogue-to-digital converter (hereinafter, referred to as an A-D converter) 42, a threshold processing unit 43, a threshold determination unit 44, a storage unit 45, and a gain controller 46. The threshold determination unit 44 includes a data processing section 441 and a data analysis section 442. The storage unit 45 includes a frequency count storage area 451.

The amplifier 41 amplifies the analogue voltage signal inputted from the photomultiplier tube 3 and outputs the amplified voltage signal to the A-D converter 42. The A-D converter 42 converts the analogue voltage signal inputted from the amplifier 41 to a digital voltage signal by sampling with a predetermined clock frequency and outputs the obtained digital voltage signal to the data processing section 441 and threshold value processing section 43. The digital voltage signal is a digital detection signal.

The storage unit 45 is composed of a RAM (random access memory) or the like and includes the frequency count storage area 451 storing the number of occurrences in association with a crest value of each pulse in the process of detecting the amount of light.

The data processing section 441 detects pulses from the digital voltage signal inputted from the A-D converter 42 based on various settings from the PC 5 and stores the frequency count of the crest value of each detected pulse in the frequency storage area 451 in association with the crest value.

The data analysis section 442 analyses the frequency counts which are stored in the frequency count storage area in association with the crest values based on the various settings from the PC 5 and determines the pulse determination threshold (crest value) used to discriminate the noise component from the signal component of the amount of light. The data analysis section 442 outputs the determined pulse determination threshold to the threshold processing unit 43.

The threshold processing unit 43 classifies the digital voltage signals inputted from the A-D converter 42 into noise pulses and light amount signal pulses based on the pulse determination threshold inputted from the data analysis section 442 and outputs the light amount signal pulses to the PC 5.

The gain controller 46 controls the intensity of the light from the light source 1 and gains of the photomultiplier tube 3 and amplifier 41 based on the various settings from the PC 5. The PC 5 includes a CPU (central processing unit) and is composed of a typical personal computer equipped with an input means such as a keyboard and a mouse and a display means such as a display. The PC 5 sets the various settings inputted using the input means in the gain controller 46, data processing section 441, and data analysis section 442 and analyses the light amount signal pulses inputted from the threshold processing unit 43. The PC 5 displays the analysis result through the display means like a display screen 51, for example.

Figure 6:
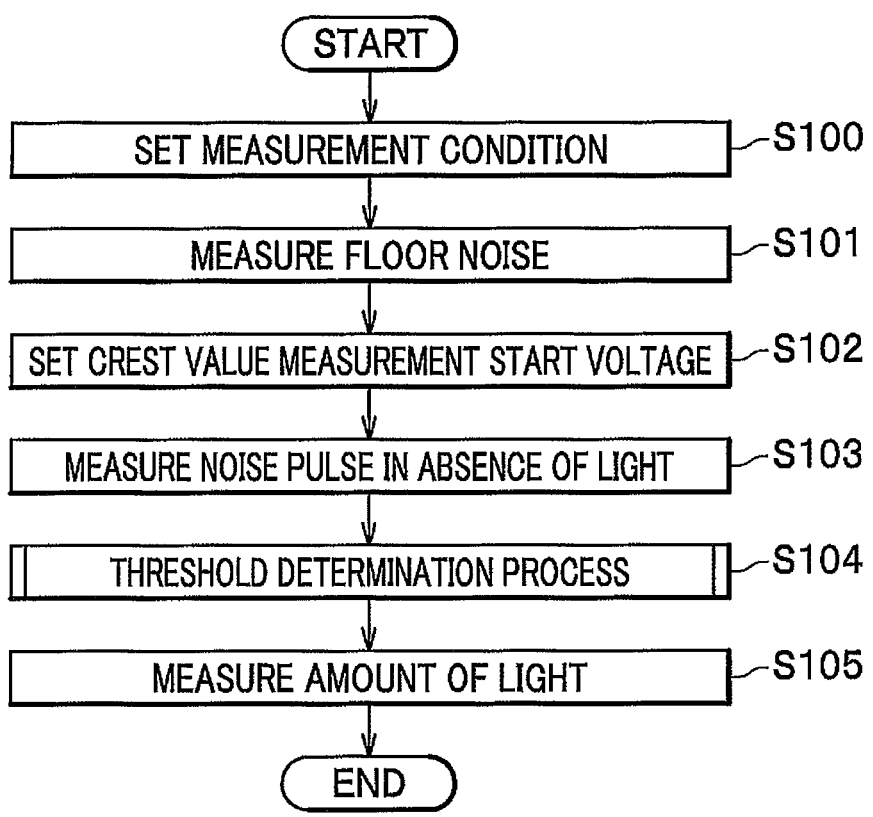
FIG. 6 is a flowchart illustrating a procedure to measure a sample using the light amount detecting device of Embodiment 1.

FIG. 6 is a flowchart illustrating a procedure to measure a sample using the light amount detecting device of Embodiment 1. First, the measurer inputs the measurement conditions by using the input function of the PC 5. The PC 5 sets the measurement conditions based on the inputted measurement conditions (step S100). To be specific, the PC 5 sets the gain control values of the amplifier 41 and photomultiplier tube 3 and the setting of light intensity of the light source 1 in the gain controller 46.

Next, the light amount detecting device starts measurement of floor noise (step S101). To be specific, the measurer turns off the power supply of the photomultiplier tube 3 and turns on the light source 1 and the power supply of the light signal detecting circuit 4. The measurer inputs an instruction to start measurement by using the input means of the PC 5. Upon receiving the instruction to start measurement, the PC 5 starts the operation of the light signal detecting circuit 4. This enables measurement of floor noise which is a noise component from the amplifier 41, A-D converter 42, and the like in the light signal detecting circuit 4. In the measurement of floor noise at the step S101, the sample 2 may be either placed or not placed in the light amount detecting device. Herein, the sample 2 is not placed.

To be more specific, the amplifier 41 amplifies the analogue voltage signal inputted from the photomultiplier tube 3 and outputs the amplified analogue voltage signal to the A-D converter 42. The A-D converter 42 converts the analogue voltage signal inputted from the amplifier 41 into digital voltage signal by sampling with a predetermined clock frequency. The A-D converter 42 then outputs the obtained digital voltage signal to the data processing section 441 and threshold processing unit 43.

Generally, floor noise is often circuit-specific. The circuit noise of the light signal detecting circuit 4 has a characteristic close to the Gaussian distribution with the referential voltage set to the voltage (normally, 0 V) in the absence of signal (where the photomultiplier tube 3 is off). The measurement of floor noise at the step S101 is performed to confirm the characteristic thereof. Accordingly, it is unnecessary to operate the threshold determination unit 44 during the measurement of floor noise.

The pulse determination threshold that the data analysis section 442 outputs to the threshold processing unit 43 is previously set to a predetermined value (for example, 0) by the PC 5 in the step S100. The digital voltage signal as the output from the A-D converter 42 is therefore directly outputted through the threshold processing section 43 to the PC 5 and can be confirmed through the display means of the PC 5. The PC 5 may display the inputted digital voltage signal directly or may display the same after processing the same in a predetermined manner.

Next, the PC 5 sets a crest value measurement start voltage value in the data processing section 441 (step S102). Herein, the crest value measurement start voltage value is a voltage serving as a criterion to determine in a later-described threshold determination process whether to count the occurrences of the crest value of interest, that is, whether to set the crest value of interest as a target crest value whose frequency distribution is stored. As described using FIG. 1, the crest values in the floor noise region are smaller than the crest values in the dark-current noise region A. Accordingly, when it is for storing (only) the frequency distribution of crest values larger than the crest value measurement start voltage value, the frequency count storage area 451 can be reduced in size. Moreover, the amount of data processed in the following processes is reduced, and the processing time can be therefore shortened.

To be specific, the measurer determines the crest value measurement start voltage value from the result of measurement of floor noise and inputs the determined crest value measurement start voltage value by using the input means of the PC 5. The PC 5 notifies the data processing section 441 of the inputted crest value measurement start voltage value. The data processing section 441 stores the received crest value measurement start voltage value.

Next, the light amount detecting device starts measurement of noise pulses in the absence of light (step S103). To be specific, the measurer turns off the light source 1 and turns on the power supplies of the photomultiplier tube 3 and light signal detecting circuit 4. The measurer then inputs an instruction to start measurement by using the input means of the PC 5. The instruction to start measurement includes sampling time for pulse detection, measurement time of pulse occurrence frequency, time to determine the pulse determination threshold, the frequency lower limit TH1 for determining the pulse determination threshold, and the like. Herein, the sampling time is each time unit at which the analogue voltage signal from the A-D converter 42 is sampled in order to detect a pulse from the analogue voltage signal. The measurement time is a time period for which the process to detect the occurrence frequency of each crest value as the maximum voltage of each pulse is executed to determine the pulse determination threshold.

Upon receiving the instruction to start measurement, the PC 5 notifies the data processing section 441 of the sampling time and the measurement time of pulse occurrence frequency. The data processing section 441 starts measurement of the sampling time and the measurement time of pulse occurrence frequency by using a not-shown time counting function. The PC 5 notifies the data analysis section 442 of the pulse determination threshold determination time to determine the pulse determination threshold and the frequency lower limit TH1. The data analysis section 442 starts measurement of the pulse determination threshold determination time using a not-shown time counting function and stores the frequency lower limit TH1. The amplifier 41 amplifies the analogue voltage signal inputted from the photomultiplier tube 3 and outputs the amplified voltage signal to the A-D converter 42. The A-D converter 42 converts the analogue voltage signal inputted from the amplifier 41 into digital voltage signal by sampling with the predetermined clock frequency and outputs the obtained digital voltage signal to the data processing section 441 and threshold processing unit 43.

Upon receiving the digital voltage signal, the threshold determination unit 44, which is composed of the data processing section 441 and data analysis section 442, executes the threshold determination process to determine the pulse determination threshold and outputs the determined pulse determination threshold to the threshold processing unit 43 (step S104). Step S105 is described later.

Figure 7:
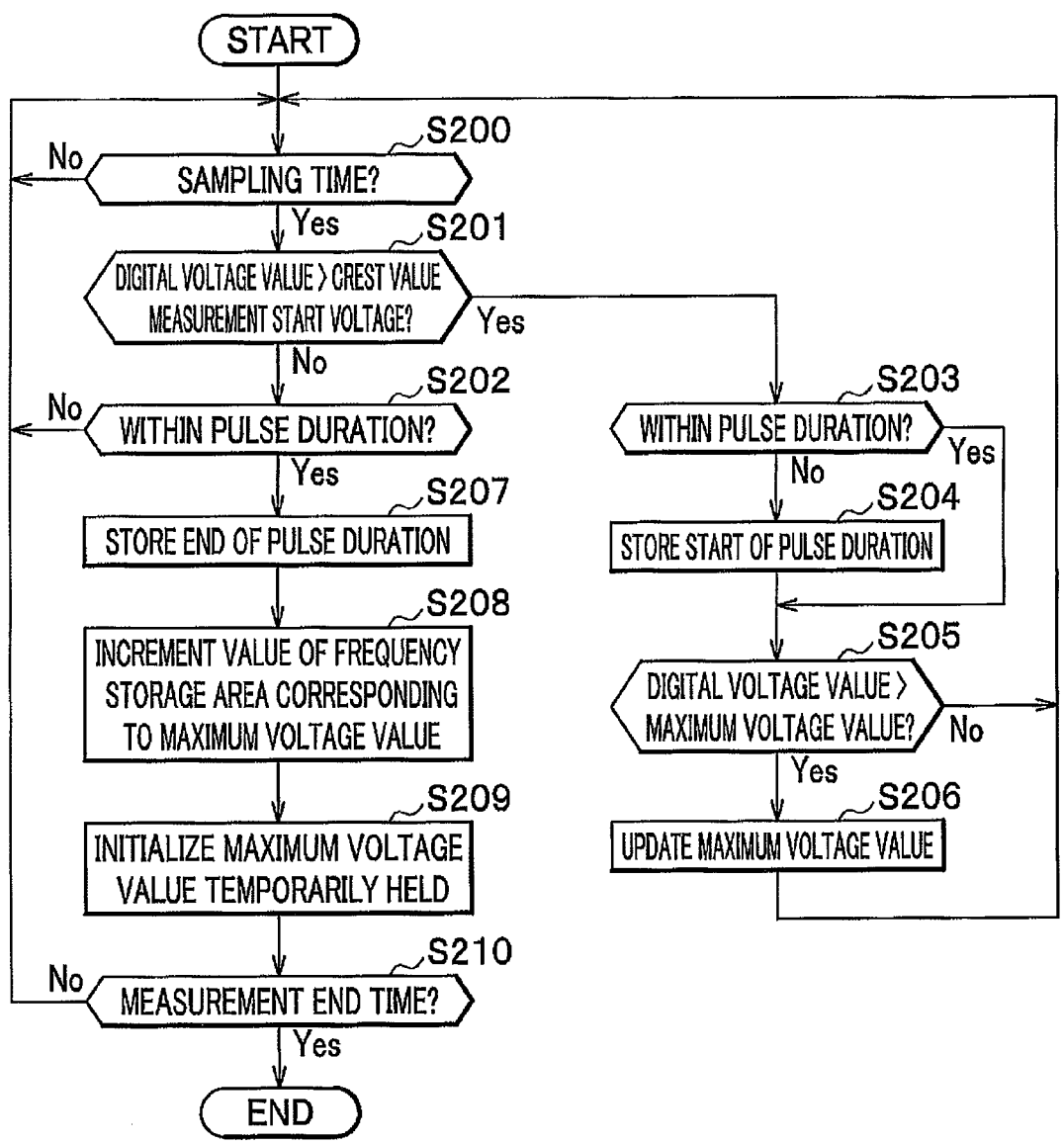
FIG. 7 is a flowchart for explaining the operation of data processing.

The threshold determination process includes data processing executed by the data processing section 441 and first data analysis processing executed by the data analysis section 442. FIG. 7 is a flowchart for explaining the operation of the data processing. The operation of the data processing executed by the data processing section 441 is described using FIG. 7.

First, when the sampling time set from the PC 5 comes (Yes in step S200), the data processing section 441 compares the digital voltage indicated by the digital voltage signal inputted from the A-D converter 42 with the crest value measurement start voltage value set from the PC 5 (step S201). When the digital voltage value is not higher than the crest value measurement start voltage value (No in the step S201), the data processing section 441 determines whether the current sampling time is in a duration where a pulse is being detected (a pulse duration). The data processing section 441 determines whether the current sampling time is in the pulse duration based on a pulse duration flag, for example, which is on when the current time is in the pulse duration and is off when the current time is not in the pulse duration. When the current sampling time is not in the pulse duration (No in the step S202), the data processing section 441 returns to the step S200 and suspends the processing until the next sampling time. The data processing section 441 also suspends the processing until the next sampling time when the current time is not the sampling time (No in the step S200).

When the digital voltage value is higher than the crest value measurement start voltage value (Yes in the step S201), the data processing section 441 determines whether the current sampling time is in the pulse duration (step S203). When the current sampling time is not in the pulse duration (No in the step S203), the data processing section 441 turns on the pulse duration flag and stores start of the pulse duration (step S204).

After the pulse duration flag is turned on or when it is determined that the current sampling time is in the pulse duration (Yes in the step S203), the data processing section 441 compares the digital voltage value inputted from the A-D converter 42 with the stored maximum voltage value (step S205). When the digital voltage value is higher than the maximum voltage value (Yes in step S205), the data processing section 441 holds the digital voltage value as the maximum voltage value to update the maximum voltage value (step S206). After the maximum voltage value is updated or when the digital voltage value is not higher than the maximum voltage value (No in step S205), the data processing section 441 returns to the step S200 and suspends the processing until the next sampling time.

On the other hand, when it is determined in the step S202 that the current sampling time is in the pulse duration (Yes in the step S202), the data processing section 441 turns off the pulse duration flag and stores the end of the pulse duration (step S207). The data processing section 441 increments the value of the frequency count storage area 451 associated with the maximum voltage value (step S208). To be specific, the data processing section 441 reads the maximum voltage value and reads the value of the frequency count storage area 451 associated with the read maximum voltage value. The data processing section 441 adds 1 to the read value and stores the incremented value in the frequency count storage area 451 in association with the maximum voltage value. The number of occurrences of the crest value which is the maximum voltage value of the detected pulse is thereby updated.

The data processing section 441 initializes the maximum voltage value (to 0 herein) (step S209). The data processing section 441 repeats the data processing (the steps S200 to S209), which detects the crest value of the pulse of interest in the pulse duration in which a digital voltage value higher than the crest value measurement start voltage value is detected, increments the value of the frequency count storage area 451 associated with the detected crest value, and stores the frequency count of the crest value of interest, until the measurement end time. The data processing section 441 terminates the measurement when the measurement end time comes (Yes in the step S210) and returns to the step S200 and suspends the processing until the next sampling time when the current time is before the measurement end time (No in the step S210).

Figure 8B:
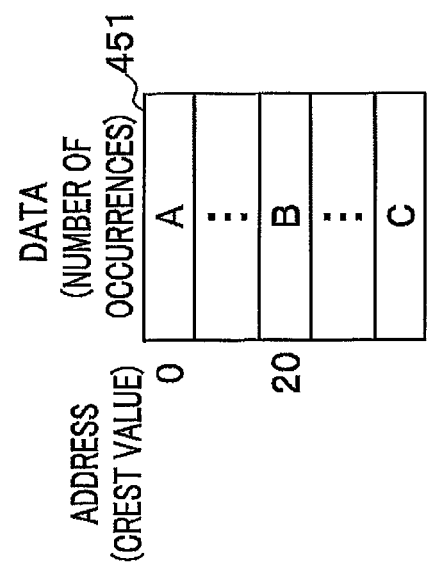
FIGS. 8A and 8B are diagrams for explaining the operation of the data processing, where
Figure 8A:
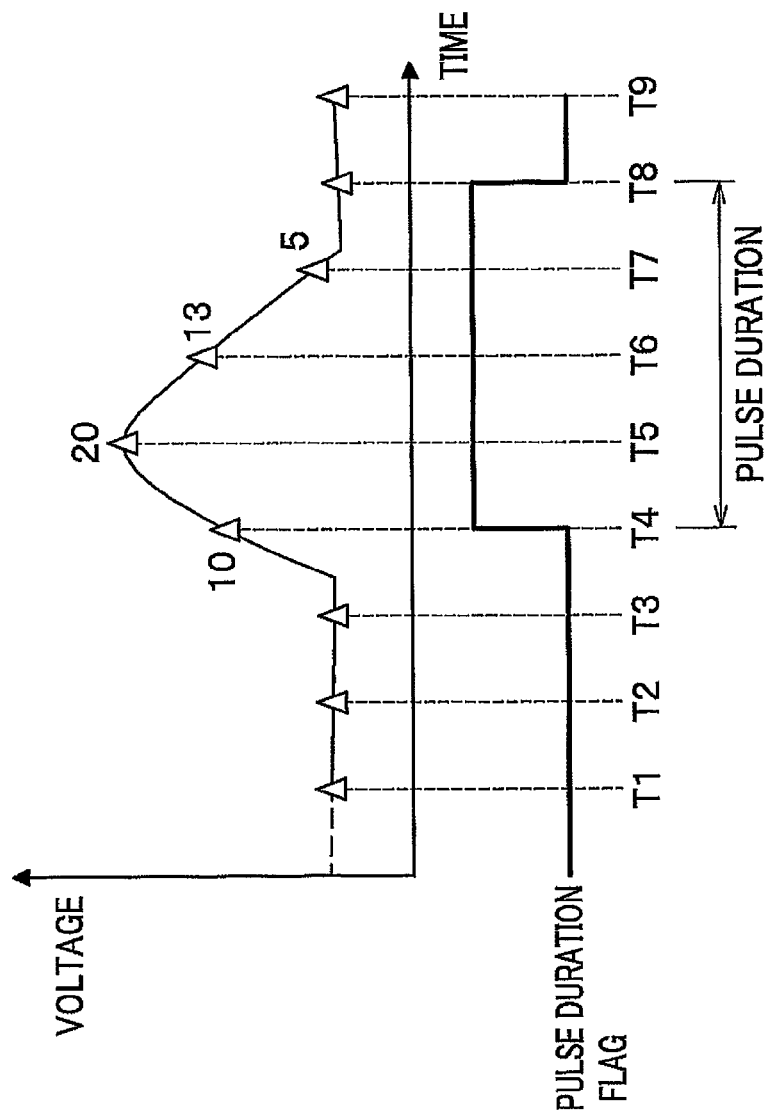

FIGS. 8A and 8B are diagrams for explaining the operation of the data processing to detect a pulse and store the frequency count of the detected pulse. In FIG. 8A, the horizontal axis represents time, and the vertical axis represents voltage. At sampling times T1 to T3 of FIG. 8A, the digital voltage values inputted from the A-D converter 42 are not higher than the crest value measurement start voltage value, and the data processing section 441 turns off the pulse duration flag.

At a sampling time T4, the digital voltage value is higher than the crest value measurement start voltage value, and the data processing section 441 turns on the pulse duration flag and stores a digital voltage value of "10" as the maximum voltage value. At a sampling time T5, the digital voltage value is 20. the data processing section 441 updates the maximum voltage vale to "20".

The digital voltage value is "13" at a sampling time T6 and is "5" at the sampling time T7. The data processing section 441 has stored "20" as the maximum voltage value since the sampling time T5. Accordingly, the data processing section 441 does not update the maximum voltage value.

At a sampling time T8, the digital voltage value is not higher than the crest value measurement start voltage value, and the data processing section 441 then turns off the pulse duration flag. In other words, the data processing section 441 determines that the detection of the pulse of interest is finished and recognizes that the maximum voltage value of the detected pulse is "20". The maximum voltage value of the detected pulse is the crest value. Accordingly, the crest value of the detected pulse is "20" in FIG. 8A.

As illustrated in FIG. 8B, in the frequency count storage area 451, addresses are defined in association with crest values. In the case of FIG. 8B, addresses 0 and 20 are respectively associated with crest values of 0 and 20, for example. For the data processing section 441 stores 20 as the maximum voltage value, the data processing section 441 reads data "B" at the address "20" and increments the same and then stores "B+1" as the data of the address "20" in the storage unit 45.

In such a manner, the number of occurrences of each crest value of the pulses detected in a predetermined period of time from the start to end of the measurement is stored in the frequency count storage area 451 by the data processing.

Figure 9:
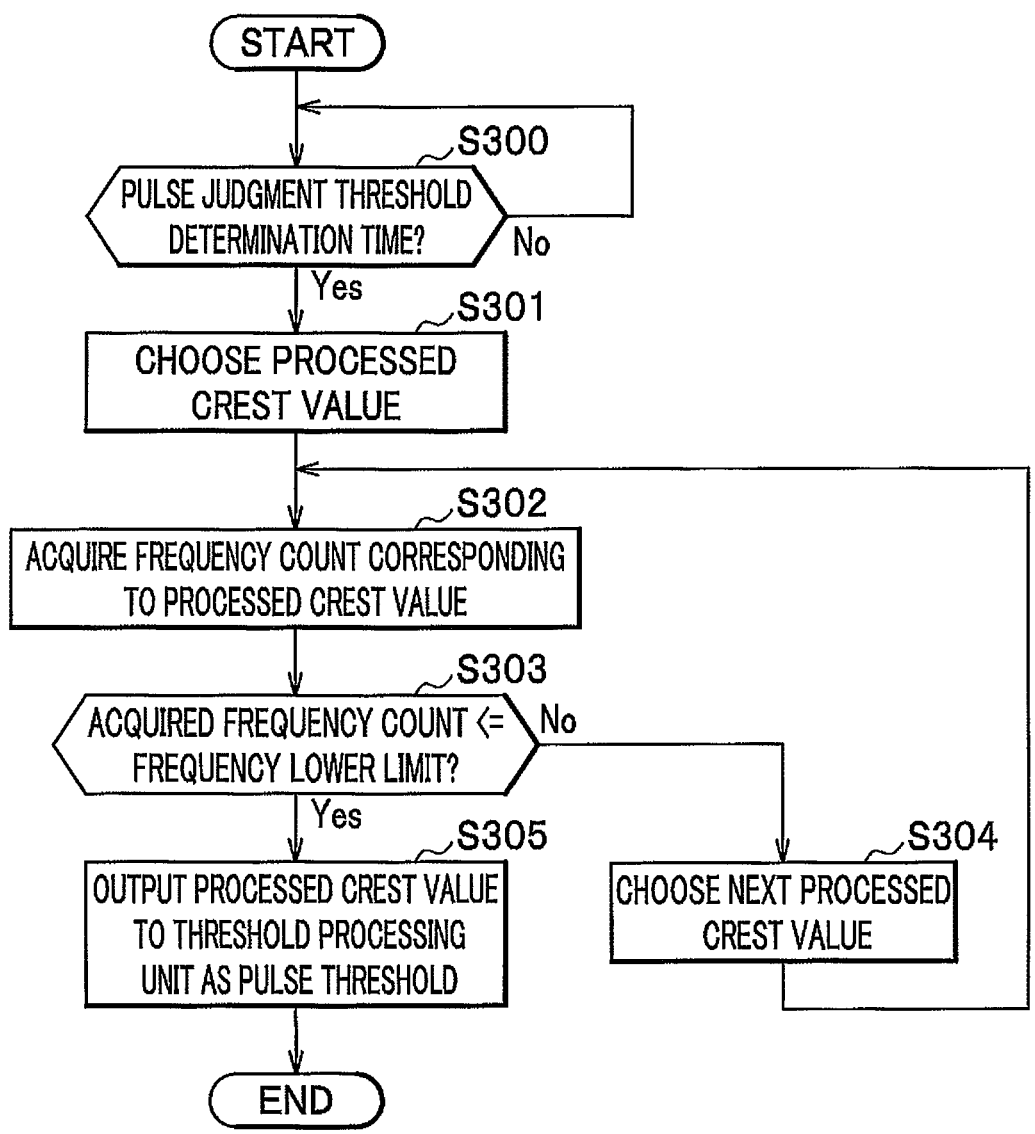
FIG. 9 is a flowchart for explaining the operation of data analysis processing.

FIG. 9 is a flowchart for explaining the operation of the first data analysis processing. The operation of the first data analysis processing executed by the data analysis section 442 is described using FIG. 9. The first data analysis processing is the threshold determination process as described above and is executed after the data processing described with reference to the flowchart of FIG. 7 above.

When the pulse determination threshold determination time comes (Yes in step S300), the data analysis section 442 chooses a processed crest value (step S301). At the first time in the processing, the data analysis section 442 chooses the smallest one of the crest values of the pulses detected by the data processing section 441 as the processed crest value. This is because the frequency of pulses having a smaller crest value is higher as described using FIG. 1. When the current time is before the pulse determination threshold determination time (No in the step S300), the data analysis section 442 suspends the processing until the pulse determination threshold determination time.

The data analysis section 442 acquires the frequency count corresponding to the processed crest value (step S302). To be specific, the data analysis section 442 acquires data of the frequency count storage area 451 associated with the processed crest value. The data analysis section 442 compares the acquired data (the frequency count) with the frequency lower limit TH1 which is set by the PC5 and stored in the data analysis section 442 (step S303).

When the acquired frequency count is higher than the frequency lower limit TH1 (No in the step S303), the data analysis section 442 chooses a next crest value to be processed (step S304). To be specific, the data analysis section 442 chooses the next highest crest value to the current processed crest value as a new processed crest value. The data analysis section 442 then repeats the operation of acquiring the frequency count corresponding to the processed crest value and compares the acquired frequency count with the frequency lower limit TH1 until the frequency count corresponding to the processed crest value becomes equal to or lower than the frequency lower limit TH1 (the steps S302 to S304).

When the acquired frequency count is equal to or lower than the frequency lower limit TH1 (Yes in the step S303), the data analysis section 442 outputs the processed crest value to the threshold processing unit 43 as the pulse determination threshold (step S305) and terminates the first data analysis processing.

Back to FIG. 6, when the threshold determination process in the step S104 is finished, the light amount detecting device starts light amount measurement for the sample 2 (step S105). To be specific, the measurer turns on all the power supplies of the power source 1, photomultiplier tube 3, and light signal detecting circuit 4 and places the sample 2 in the light amount detecting device. The measurer then inputs an instruction to start the light amount measurement of the sample 2 by using the input means of the PC 5. Upon receiving the instruction to start the light amount measurement, the PC 5 notifies the light signal detecting circuit 4 and causes the same to start the measurement.

To be more specific, the amplifier 41 amplifies the analogue voltage signal F inputted from the photomultiplier tube 3 and outputs the amplified voltage signal to the A-D converter 42. The A-D converter 42 converts the analogue voltage signal inputted from the amplifier 41 by sampling with a predetermined clock frequency and outputs the obtained digital voltage signal to the data processing section 441 and threshold processing unit 43.

Upon receiving the digital voltage signal, the threshold processing unit 43 compares the voltage value indicated by the digital voltage signal with the pulse determination threshold as the voltage value outputted from the data analysis section 442. When the voltage value is not lower than the pulse determination threshold, the threshold processing unit 43 outputs the digital voltage signal inputted from the A-D converter 42 directly to the PC 5. When the voltage value is lower than the pulse determination threshold, the threshold processing unit 43 sets the digital voltage signal to 0 and outputs the same to the PC 5.

Next, the frequency lower limit TH1 is described. The frequency lower limit TH1 is set to a value higher than the boundary between the floor noise region and the dark current noise region A illustrated in FIG. 1 above based on actually measured values, such as the result of floor noise measurement of the step S101 illustrated in FIG. 6. The frequency lower limit TH1 is set to a frequency value satisfying a predetermined performance of the light amount detecting device, for example. The dark current noise changes depending on the temperature of the photomultiplier tube 3 and is therefore often influenced by the installation place of the light amount detecting device. Accordingly, the frequency lower limit TH1 is often specific to the installation place and may be therefore set to a value experimentally obtained.

FIGS. 10A and 10B are diagrams illustrating outputs of the light signal detecting circuit of Embodiment 1. As illustrated in Part FIG. 10A, when the frequency lower limit TH1 is set to the frequency count at the crest value H2 corresponding to the boundary between the floor noise region and dark current noise region A illustrated in FIG. 1, the pulse determination threshold is the voltage value of the crest value H2. Accordingly, the light signal detecting circuit outputs a pulse P1 due to dark current noise together with a light signal pulse.

As illustrated in FIG. 10B, when the frequency lower limit TH1 is set to a value higher than the boundary between the floor noise region and dark current noise region A, for example, the frequency count at the crest value H3 as the boundary between the dark current noise regions A and B illustrated in FIG. 1, the pulse determination threshold is the voltage value of the crest value H3. The light signal detecting circuit therefore outputs (only) the light signal pulse by removing the pulse P1 due to dark current noise.

As described above, in Embodiment 1, the data processing section 441 detects pulses from the digital voltage signal corresponding to the light amount which is converted by the amplifier 41 and A-D converter 42, calculates crest values as the maximum voltage values of the detected pulses, and stores the frequency count of each calculated crest value in the frequency count storage area 451. The data analysis section 442 compares the predetermined frequency lower limit with the number of occurrences of each crest value stored in the frequency count storage area 451 sequentially in ascending order of the crest values and, as a result of the comparison, determines the pulse determination threshold to be the crest value whose number of occurrences is equal to or smaller than the frequency lower limit. The threshold processing unit 43 is configured to output (only) the digital voltage signal not lower than the pulse determination threshold as the detection signal. Accordingly, the signal component of a small amount of light and the signal component of noise due to dark current can be discriminated with the simple operation of setting the frequency lower limit TH1.

In the light amount detecting device including the light signal detecting circuit 4 of Embodiment 1, the light signal detecting circuit 4 removes the signal of noise due to dark current, thus increasing the S/N (signal-noise ratio). Accordingly, the light amount detecting device can detect a very small amount of light.

When the occurrence frequency of crest values changes with changes in temperature, the pulse determination threshold can be changed by performing the noise pulse measurement in the absence of light in the step S103 of FIG. 6 and the threshold determination process in the step S104. Accordingly, even when the frequency counts of pulses change with changes in temperature, the pulse determination threshold can be set to a proper value, and the signal component of a small amount of light and the signal component of noise due to dark current can be discriminated in response to changes in temperature.

Moreover, the pulse determination threshold may be calculated every predetermined time during the light amount measurement by executing the threshold determination process every predetermined time. This makes it possible to determine the pulse determination threshold to be a proper value even if the frequency counts of pulses change with a change in temperature. Accordingly, even when the temperature in the measurement environment changes, the signal component of a small amount of light and the signal component of noise due to dark current can be discriminated in response to the change.

When the pulse determination threshold is changed, the data analysis section 442 may be configured to notify the PC 5. The notified PC 5 displays that the pulse determination threshold is changed or the value of the pulse determination threshold through the output means. This allows the measurer to know that the pulse determination threshold is changed or the value of the pulse determination threshold.

After determined by the threshold determination process of the step S104 of FIG. 6, the pulse determination threshold may be dynamically changed during the light amount measurement of the sample by previously representing as a function, the relation between the determined pulse determination threshold and the temperature. In this case, first, the PC 5 previously stores the function of the relation between the pulse determination threshold and temperature in the data analysis section 442. Moreover, the light amount detecting device is provided with a sensor detecting temperature and notifies the data analysis section 442 of the light signal detecting circuit 4 of the detected temperature. The data analysis section 442 only needs to determine the pulse determination threshold based on the temperature transmitted from the sensor and the function of the relation between the stored pulse determination threshold and temperature.

Embodiment 2

Figure 11:
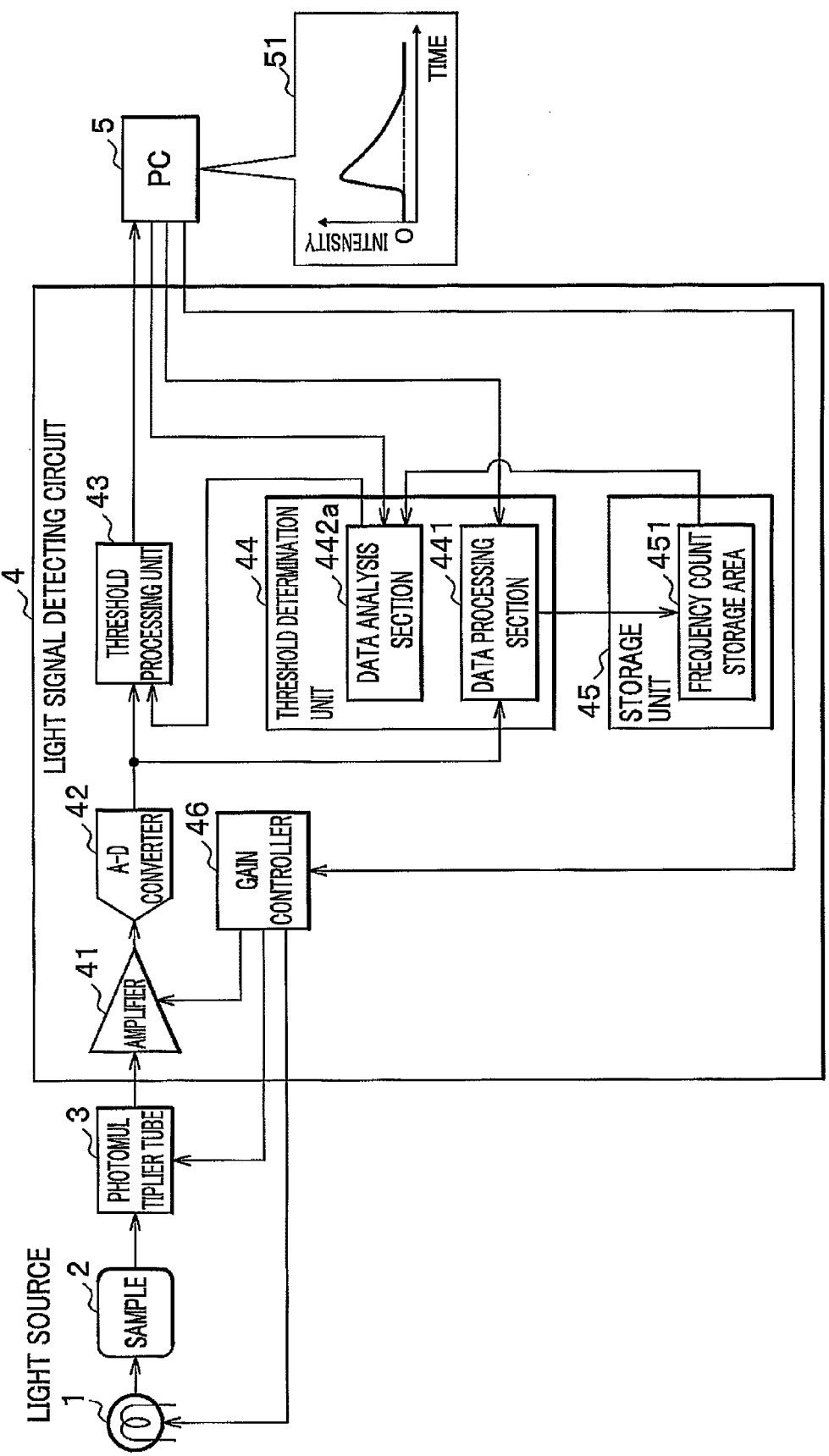
FIG. 11 is a block diagram illustrating the configuration of a light amount detecting device including a light signal detecting circuit of Embodiment 2 of the present invention.
Figure 12:
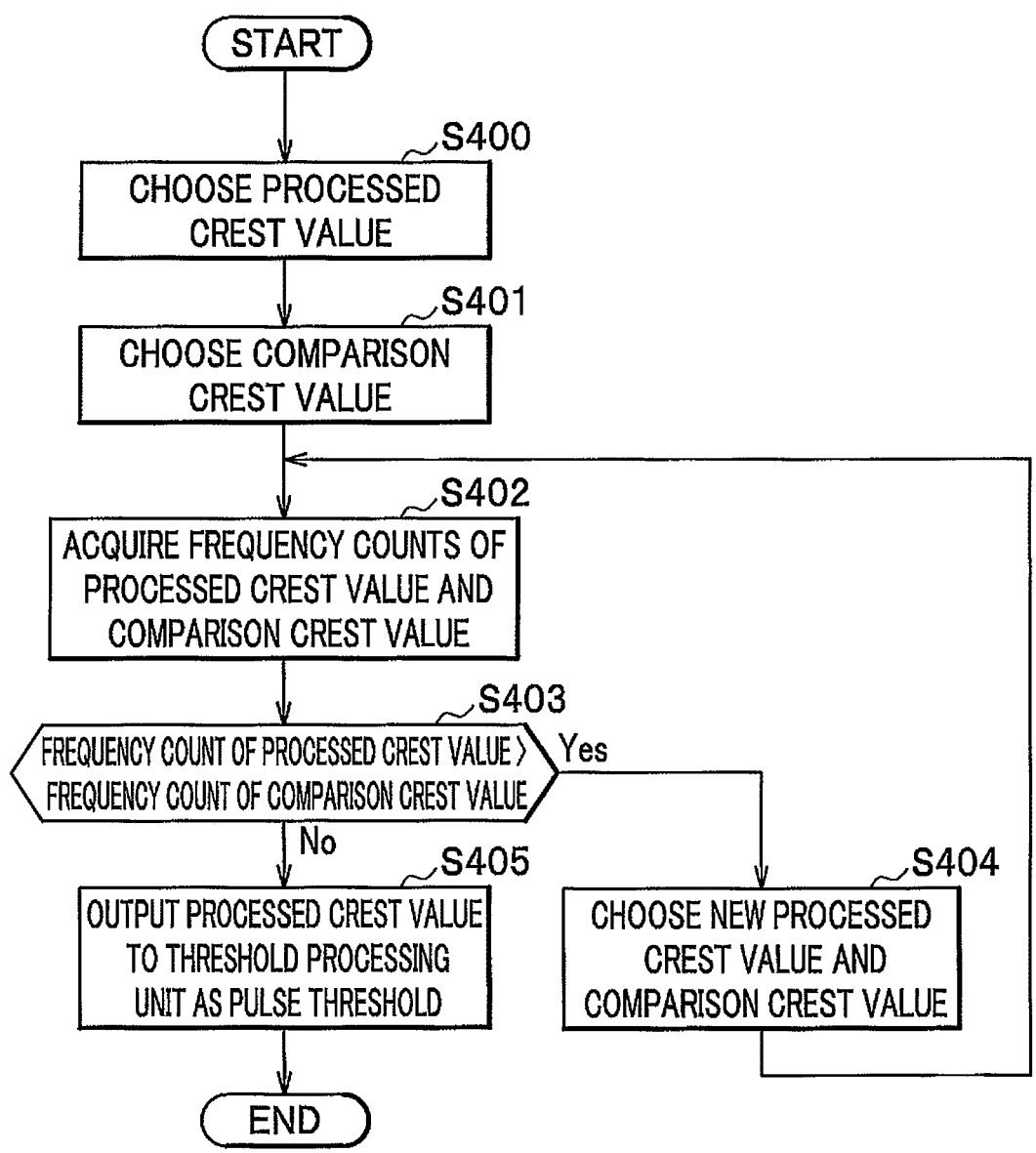
FIG. 12 is a flowchart for explaining the operation of second data analysis processing.

Embodiment 2 of the present invention is described using FIGS. 11 and 12. FIG. 11 is a block diagram illustrating the configuration of a light amount detecting device including a light signal detecting circuit of Embodiment 2 of the present invention. The light amount detecting device of Embodiment 2 illustrated in FIG. 11 is substantially the same as the light amount detecting device of Embodiment 1 illustrated in FIG. 5 above. The light amount detecting device of Embodiment 2 differs from that of Embodiment 1 in including a data analysis section 442a instead of the data analysis section 442 of the threshold determination unit 44 of the light signal detecting circuit 4. The constituent components having the same functions as those of the light amount detecting device of Embodiment 1 are given same reference numerals, and the description thereof is omitted.

In addition to the function of the data analysis section 442, the data analysis section 442a includes a function to analyze the occurrence frequency stored in association with each crest value and determine the pulse determination threshold to be the crest value whose occurrence frequency is the smallest.

Next, the operation of the light amount detecting device of Embodiment 2 is described. The operation of the light amount detecting device of Embodiment 2 is substantially the same as that of the light amount detecting device of Embodiment 1 above and differs from the same in further including second data analysis processing performed by the data analysis section 442a during the light amount detection. Herein, only the operation of the second data analysis processing is described.

The operation of the second data analysis processing is performed during the light amount measurement in the step S105 illustrated in FIG. 6 above. It is assumed that the data processing section 441 performs the operation of the data processing described in the flowchart of FIG. 7 above during the light amount measurement in the step S105.

FIG. 12 is a flowchart for explaining the operation of the second data analysis processing. When the pulse determination threshold determination time comes, the data analysis section 442a chooses a processed crest value (step S400). To be specific, the data analysis section 442a chooses as the processed crest value, the smallest one of the crest values of the pulses detected by the data processing section 441.

Next, the data analysis section 442a chooses a comparison crest value (step S401). To be specific, the data analysis section 442a chooses as the comparison crest value, the next highest crest value to the processed crest value.

The data analysis section 442a acquires the frequency counts of the processed crest value and the comparison crest value (step S402). To be specific, the data analysis section 442a acquires data (frequency counts) in the frequency count storage area 451 associated with the processed crest value and the comparison crest value. The data analysis section 442a compares the acquired frequency count of the processed crest value with the acquired frequency count of the comparison crest value (step S403).

When the frequency count of the processed crest value is higher than the frequency count of the comparison crest value (Yes in the step S403), the data analysis section 442a chooses a new processed crest value and a new comparison crest value (step S404). To be specific, the current comparison crest value is chosen as the new processed crest value, and the next largest crest value to the new processed crest value is chosen as the new comparison crest value. The data analysis section 442a returns to the step S402 and acquires the frequency counts of the processed crest value and the comparison crest value from the frequency count storage area 451 for comparing the acquired frequency count of the processed crest value with the acquired frequency count of the comparison crest value.

When the frequency count of the processed crest value is not higher than the frequency count of the comparison crest value (No in the step S403), the data analysis section 442a outputs the value of the processed crest value to the threshold processing unit 43 as the pulse determination threshold value (step S405) and terminates the second data analysis processing.

As described above, in Embodiment 2, the data processing section 441 detects pulses from the digital voltage signal corresponding to an amount of detected light which is converted by the amplifier 41 and A-D converter 42; calculates the crest values as the maximum voltage values of the detected pulses; and store the occurrence frequency of each detected crest value in the frequency count storage area 451. The data analysis section 442a calculates the smallest one of the frequency counts of the crest values which are stored in the frequency count storage area 451 in association with the crest values by comparing the frequency count of each crest value in ascending order of the crest values and sets the pulse determination threshold to the crest value whose frequency count is the smallest frequency count. The threshold processing unit 43 is configured to output (only) the digital voltage signal not lower than the pulse determination threshold as the detection signal. Even when the frequency counts of pulses change with a change in temperature, the pulse determination threshold can be therefore set to a proper value, and the signal component of a small amount of light and the signal component of noise due to dark current can be discriminated in response to the change in temperature.

In the light amount detecting device including the light signal detecting circuit 4 of Embodiment 2, the light signal detecting circuit 4 removes the signal of noise due to dark current, so that the S/N (signal-noise ratio) can be increased. Accordingly, the light amount detecting device can detect a very small amount of light.

In Embodiment 2, the pulse determination threshold is set to the crest value whose frequency count is the smallest frequency count. However, the pulse determination threshold may be set to a crest value a predetermined value larger or smaller than the smallest crest value. In this case, the predetermined value, by which the crest value is smaller or larger, is previously set in the data analysis section 442a from the PC 5, and a value obtained by reducing or adding the predetermined value from or to the smallest crest value is set as the pulse determination threshold value.

In the light signal detecting circuit 4 of Embodiment 2, the data processing section 441 acquires the occurrence frequency count of each crest value by the data processing during the light amount measurement, and the data analysis section 442a determines the pulse determination threshold from the occurrence frequency count of each crest value by the second data analysis processing. Accordingly, the pulse determination threshold may be determined by executing the light amount measurement of the sample 2 without executing the procedure to perform measurement of the sample of the light amount detecting device of Embodiment 1 described above. The pulse determination threshold can be therefore determined without setting the frequency lower limit TH1.

When the pulse determination threshold is changed, the data analysis section 442 may be configured to notify the PC 5. The notified PC 5 may display that the pulse determination threshold is changed or the value of the pulse determination threshold through the output means. This allows the measurer to know that the pulse determination threshold is changed or the value of the pulse determination threshold.

Embodiment 3

Embodiment 3 of the present invention is described using FIGS. 13A to 15. In the process of detecting an amount of light in Embodiments 1 and 2 described above, it is sometimes necessary to adjust the gains of the light source 1, photomultiplier tube 3, and amplifier 41. In Embodiment 3, the gain adjustment of the light source 1, photomultiplier tube 3, and amplifier 41 is described.

FIGS. 13A to 13D are diagrams for explaining the condition of gain adjustment. In FIGS. 13A and 13C, the horizontal axis represents crest values, and the vertical axis represents frequency. In FIGS. 13B and 13C, the horizontal axis represents time, and the vertical axis represents the number of pulses detected in each unit time.

A line G31 of FIG. 13A represents the relation between crest values and frequency after a predetermined period of time from the start of measurement. In the line G31, the crest value at the boundary where the decreasing frequency begins to increase, that is, the frequency of the crest value serving as the pulse determination threshold is higher than the frequency lower limit TH1. When the frequency of the crest value serving as the pulse determination threshold is higher than the frequency lower limit TH1, as illustrated in FIG. 13B, the number of pulses detected in each unit time is distributed in a proper frequency range between a proper lower limit TH6 and a proper upper limit TH7, showing a stable state. This represents that the quantization efficiency is stable, which means insufficient voltage amplification by the amplifier 41. Accordingly, when the frequency of the crest value as the pulse determination threshold is higher than the frequency lower limit TH1 and the number of pulses detected in each unit time is distributed in the proper frequency range between the proper lower and upper limits TH6 and TH7, it is preferable that the gain of the amplifier 41 is adjusted so that the frequency of the crest value as the pulse determination threshold is lower than the frequency lower limit TH1 as represented by a line G32 of FIG. 13A.

A line G33 of FIG. 13C represents the relation between crest values and frequency after a predetermined period of time from the start of measurement. In the line G33, the frequency of the crest value serving as the pulse determination threshold is lower than the frequency lower limit TH1, and the frequency counts of the crest values distributed about the crest value determined by the multiplying characteristic of the photomultiplier tube 3 are also lower than the frequency lower limit TH1. In such a case, as illustrated in FIG. 13D, the number of pulses detected in each unit time is not distributed in the proper frequency range between the proper lower and upper limits TH6 and TH7 and is equal to or lower than the proper lower limit TH6. This represents insufficient voltage of the photomultiplier tube 3, and it is preferable that the voltage of the photomultiplier tube 3 is adjusted (gain-adjusted) so that the frequency counts of the crest values distributed about the crest value determined by the multiplying characteristic of the photomultiplier tube 3 are also higher than the frequency lower limit TH1.

In the light of the aforementioned matters, in Embodiment 3, the number of pulses detected in each unit time is counted, and based on the counted number of pulses and pulse determination threshold, the gains of the light source 1, photomultiplier tube 3, and amplifier 41 are adjusted.

Figure 14:
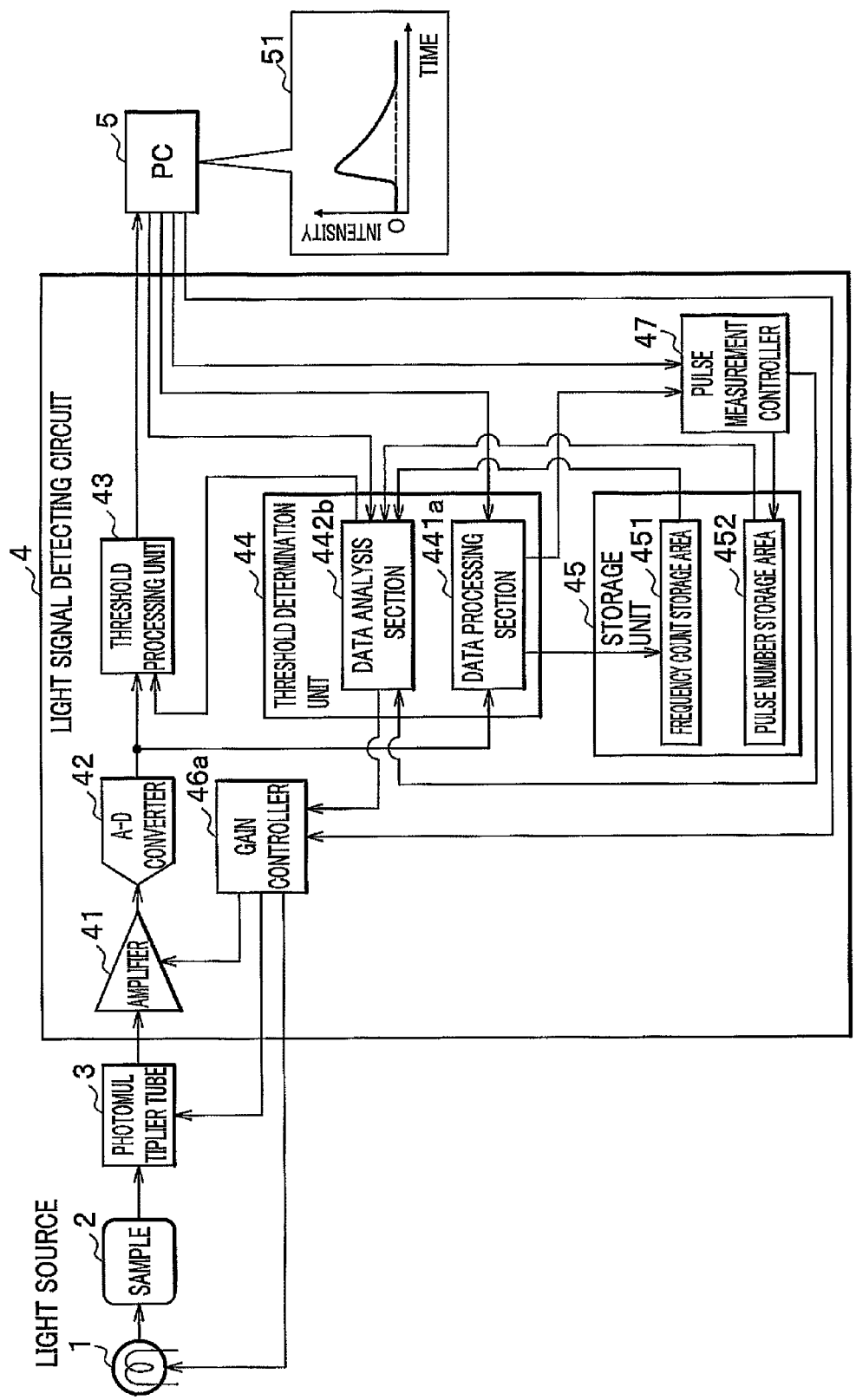
FIG. 14 is a block diagram illustrating the configuration of the light amount detecting device including a light signal detecting circuit of Embodiment 3 of the present invention.

FIG. 14 is a block diagram illustrating the configuration of the light amount detecting device including the light signal detecting circuit of Embodiment 3 of the present invention. The light amount detecting device including the light signal detecting circuit of Embodiment 3 of the present invention illustrated in FIG. 14 further includes the a pulse number storage area 452 in the storage unit 45 of the light signal detecting circuit 4 of the light amount detecting device including the light amount detecting circuit of Embodiment 2 illustrated in FIG. 11 and further includes a pulse measurement controller 47. Moreover, the light amount detecting device of Embodiment 3 includes a data processing section 441a, a data analysis processing section 442b, and a gain controller 46a instead of the data processing section 441, data analysis processing section 442a, and gain controller 46, respectively. The constituent components having the same functions as those of the light amount detecting device of Embodiment 1 are given the same reference numerals, and the redundant description thereof is omitted.

In addition to the function of the data processing section 441, the data processing section 441a outputs a pulse detection notification, which gives a notice of detection of a pulse, to the pulse measurement controller 47 each time that the frequency count of the frequency count storage area 451 is updated.

The pulse measurement controller 47 controls the unit time for the pulse measurement set by the PC 5, the time to determine gain adjustment, and the like. The pulse measurement controller 47 counts the pulse detection notifications received in each unit time and stores the number of counts in the pulse number storage area 452.

The data analysis section 442b is notified by the pulse measurement controller 47 and determines whether to perform gain adjustment in addition to the function of the data analysis section 442a. The determination is described later with reference to FIG. 15. The data analysis section 442b outputs a gain adjustment notification to the gain controller 46a when the gain adjustment is necessary as a result of the determination. Upon receiving the gain adjustment notification, the gain controller 46a adjusts the gains of the light source 1, photomultiplier tube 3, and amplifier 41.

Next, the operation of the light amount detecting device of Embodiment 3 is described. The operation of the light amount detecting device of Embodiment 3 to determine the pulse determination threshold is the same as that of the threshold determination process of Embodiment 1 or 2. Separately from the threshold determination process, the operation of the gain adjustment determination process described below is performed. Herein, only the operation concerning the gain adjustment performed during the light amount detection is described.

After updating the maximum voltage value in the step S206 of the data processing described using the flowchart of FIG. 7, the data processing section 441a outputs a pulse detection notification, which gives a notice of detection of the pulse, to the pulse measurement controller 47.

When receiving the pulse detection notification, the pulse measurement controller 47 repeats the operation of counting up the value of a not-shown pulse counter until the unit time previously set is finished. When the unit time is finished, the pulse measurement controller 47 stores the value of the pulse counter in the pulse number storage area 452. The pulse measurement controller 47 then initializes the value of the pulse counter (set to 0) and counts up the value of the pulse counter in the next unit time.

In the pulse number storage area 452, the addresses are associated with the respective unit times. The value of the pulse counter (number of pulses) in each unit time is stored at the corresponding address.

When the gain adjustment determination time comes, the pulse measurement controller 47 notifies the data analysis section 442b. When notified that the gain adjustment determination time comes, the data analysis section 442b executes the gain adjustment determination process.

Figure 15:
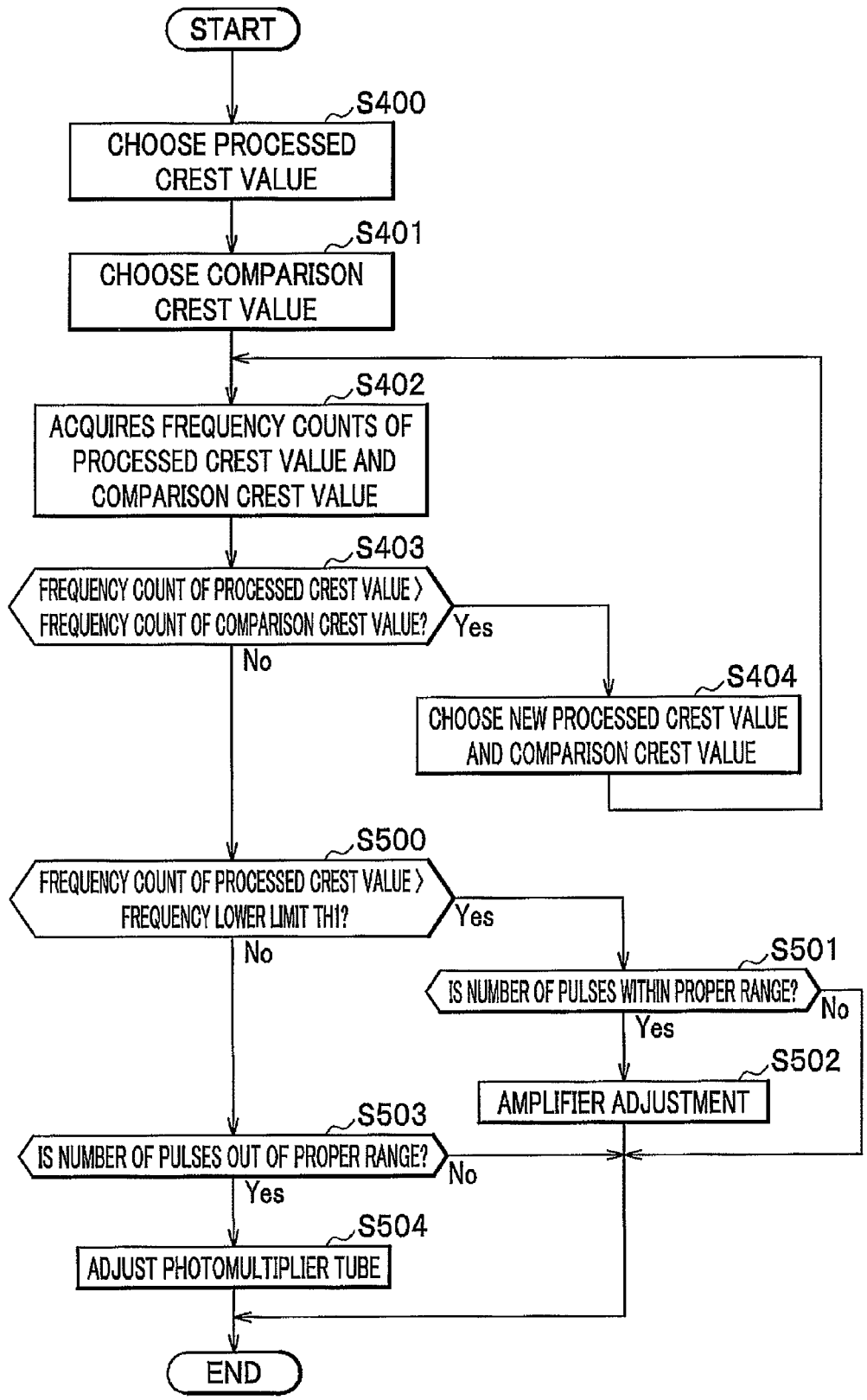
FIG. 15 is a flowchart for explaining the operation of a gain adjustment determination process.

FIG. 15 is a flowchart for explaining the operation of the gain adjustment determination process. With reference to the flowchart of FIG. 15, the operation of the gain adjustment determination process is described in detail. The process to calculate the smallest value of the frequency of crest values is the same as the process by the steps S400 to S404 described in the flowchart of FIG. 12. Accordingly, the steps of the process are given the same reference numerals, and the detailed description is omitted.

The data analysis section 442b chooses a processed crest value and a comparison crest value (steps S400 and S401). The data analysis section 442b acquires the frequency counts of the processed crest value and comparison crest value (step S402). The data analysis section 442b compares the acquired frequency count of the processed crest value with the acquired frequency count of the comparison crest value (step S403). When the frequency count of the processed crest value is higher than the frequency count of the comparison crest value (Yes in the step S403), the data analysis section 442b chooses a new processed crest value and a new comparison crest value (step S404). Back to the step S402, the data analysis section 442b acquires the frequency counts of the processed crest value and comparison crest value and compares the acquired frequency count of the processed crest value with the acquired frequency count of comparison crest value.

When the frequency count of the processed crest value is not higher than the frequency count of the comparison crest value (No in the step S403), the data analysis section 442b compares the frequency of the processed crest value with the frequency lower limit TH1 (step S500). When the frequency of the processed crest value is higher than the frequency lower limit TH1 (Yes in the step S500), the data analysis section 442b determines whether the number of pulses is in the proper range (step S501).

To be specific, the data analysis section 442b acquires all the numbers of pulses which are detected in the respective unit times and are stored in the pulse number storage area 452, the data analysis section 442b determines whether the acquired number of pulses detected in each unit time is not smaller than the previously determined proper lower limit TH6 and is not larger than the previously determined proper upper limit TH7. In this case, the numbers of pulses may be determined to be in the proper range when the numbers of pulses of all the time units are equal to or larger than the proper lower limit TH6 and are equal to or smaller than the proper upper limit TH7. Alternatively, the numbers of pulses may be determined to be in the proper range if the number of pulses in each unit time not smaller than the proper lower limit TH6 and is not larger than the proper upper limit TH7 in a predetermined number of time units.

When it is determined that the numbers of pulses are in the proper range (Yes in the step S501), the data analysis section 442b outputs a gain adjustment notification to adjust the amplifier 41 to the gain controller 46a (step S502) and terminates the process. When it is determined that the numbers of pulses are not in the proper range (No in the step S501), the data analysis section 442b terminates the process.

On the other hand, when the frequency count of the processed crest value is not higher than the frequency lower limit TH1 (No in the step S501), the data analysis section 442b determines whether the numbers of pulses are out of the proper range (step S503). To be specific, the data analysis section 442b acquires all of the numbers of pulses which are detected at the respective unit times and are stored in the pulse number storage area 452. The data analysis section 442b then determines whether each acquired number of pulses is not smaller than the previously determined proper lower limit TH6 and is not larger than the previously determined proper upper limit TH7. In this case, for example, the number of pulses may be determined to be out of the proper range when the numbers of pulses in all the time units are equal to or larger than the proper lower limit TH6 and are equal to or smaller than the proper upper limit TH7. Alternatively, the number of pulses may be determined to be out of the proper range if the number of pulses is equal to or smaller than the proper lower limit TH6 or is equal to or larger than the proper upper limit TH7 in the predetermined number of time units.

When the number of pulses is determined to be out of the proper range (Yes in the step S503), the data analysis section 442b outputs a gain adjustment notification indicating adjustment of the voltage of the photomultiplier tube 3 to the gain controller 46a (step S504) and terminates the process. When the number of pulses is determined to be in the proper range (No in the step S503), the data analysis section 442b terminates the process.

Upon receiving the gain adjustment notification by the above-described gain adjustment determination process, the gain controller 46a adjusts the amplifier 41 or photomultiplier tube 3 based on the received gain adjustment notification. The amount of adjustment should be determined by experiments or the like in advance and should be set in the gain controller 46a through the PC 5. Moreover, the gain controller 46a may be configured to adjust not only the photomultiplier tube 3 but also the light source 1.

As described above, in Embodiment 3, the pulse measurement controller 47 counts the number of pulses detected by the data processing section 441a and stores the counted numbers of pulses in association with respective unit times in the pulse number storage area. The data analysis section 442b calculates the smallest one of the numbers of occurrences of the crest values which are stored in the frequency count storage area 451 in association with the crest values by comparing the number of occurrences of each crest value in ascending order of the crest values and determines whether to adjust the gains of the amplifier 41 and photomultiplier tube 3 based on the calculated smallest number of occurrences, frequency lower limit TH1, and the number of pulses which are detected in each unit time and stored in the pulse number storage area 452. The gain controller 46a adjusts the gains of the amplifier 41 and photomultiplier tube 3 based on the determination result. Accordingly, the light amount detecting device can be controlled including controlling the gains of the amplifier 41 and photomultiplier tube 3, thus more appropriately discriminating the signal component of a very small amount of light from the signal component of noise due to dark current.

Embodiment 4

Figure 16:
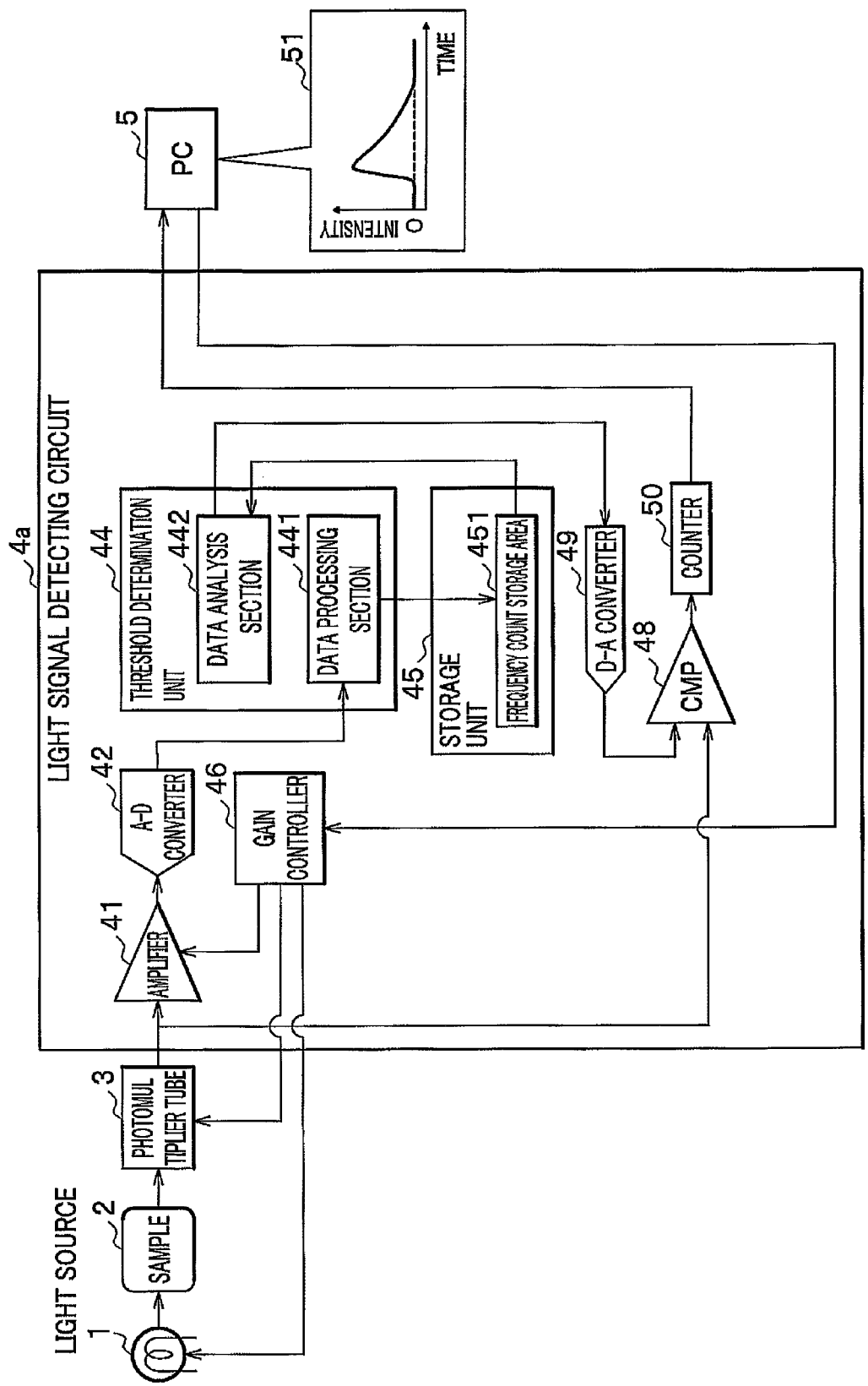
FIG. 16 is a block diagram illustrating the configuration of a light amount detecting device including a light signal detecting circuit of Embodiment 4 of the present invention.
Figure 17:
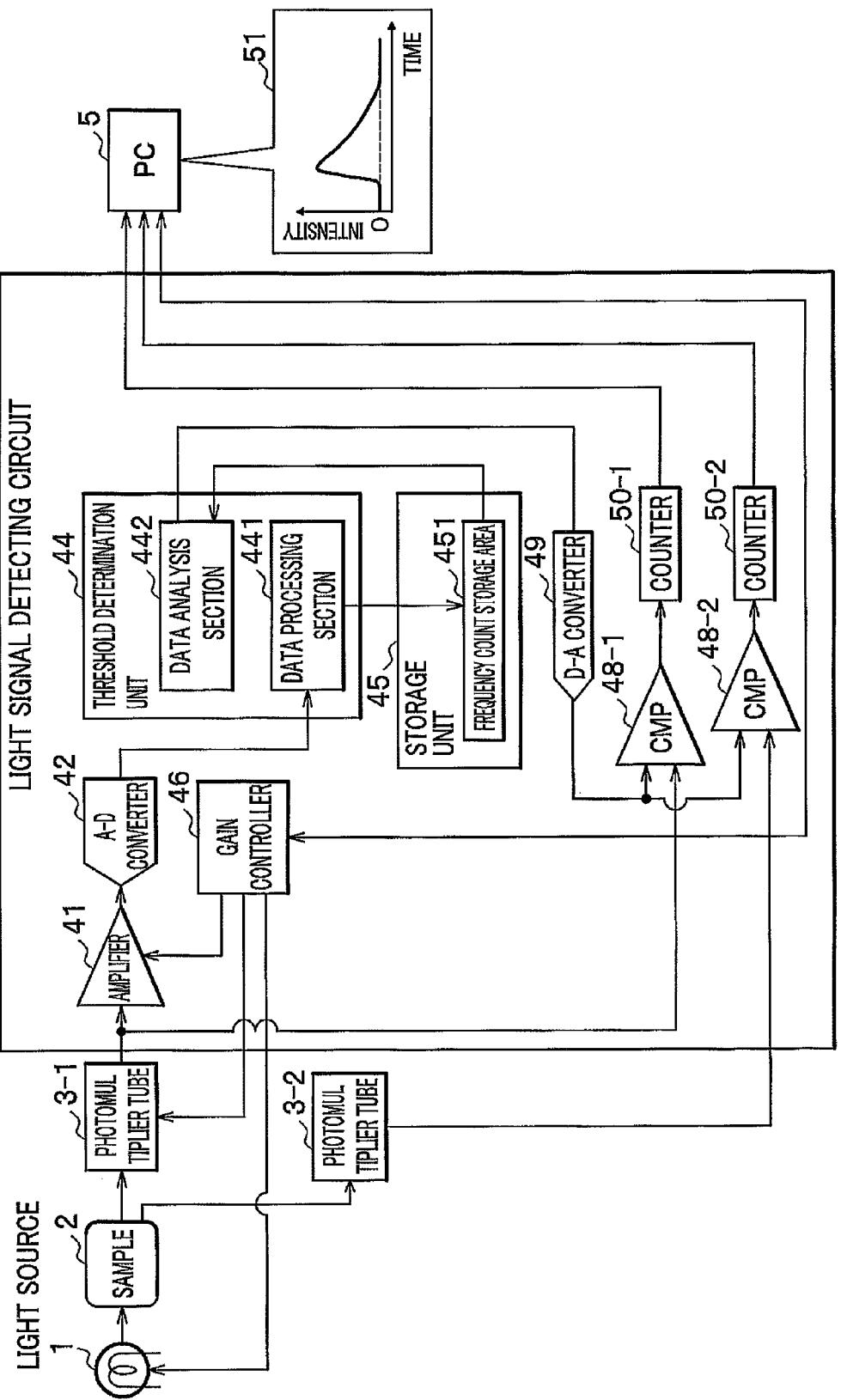
FIG. 17 is a block diagram illustrating another configuration of the light amount detecting device including the light signal detecting circuit of Embodiment 4 of the present invention.

Embodiment 4 of the present invention is described using FIGS. 16 and 17. FIG. 16 is a block diagram illustrating the configuration of a light amount detecting device including a light signal detecting circuit of Embodiment 4 of the present invention. The light amount detecting device of Embodiment 4 illustrated in FIG. 16 includes a light signal detecting circuit 4a instead of the light signal detecting circuit 4 of the light amount detecting device of Embodiment 1 illustrated in FIG. 5. The light signal detecting circuit 4a has the same configuration of the light signal detecting circuit 4 except that the light signal detecting circuit does not include the threshold processing unit 43 and further includes a digital-to-analogue converter (hereinafter, referred to as a D-A converter) 49, a comparator 48 (CMP in the drawings), and a counter 50. The constituent components of the light amount detecting device of Embodiment 4 having the same functions as those of the light amount detecting device of Embodiment 1 are given the same reference numerals, and the redundant description thereof is omitted.

The D-A converter 49 converts the pulse determination threshold inputted from the data analysis section 442 from digital data to an analogue signal (hereinafter, referred to as an analogue pulse determination threshold). The comparator 48 compares the analogue voltage signal inputted from the photomultiplier tube 3 with the analogue pulse determination threshold inputted from the D-A converter 49. (Only) when the analogue voltage is not lower than the pulse determination threshold as the result of the comparison, the comparator 48 outputs a pulse instructing to count up waveform shaping operations (a count instruction signal) to the counter 50. When receiving the count instruction signal, the counter 50 counts up the count value and outputs the count value to the PC 5.

Next, the operation of the light amount detecting circuit of Embodiment 4 is described. The procedure to perform measurement of the sample 2 using the light amount detecting device of Embodiment 4 is the same as the procedure described with reference to the flowchart of FIG. 6 above. The pulse determination threshold is determined by the data processing described with reference to the flowchart of FIG. 7 above and the data analysis processing described with reference to the flowchart of FIG. 9 above. The difference from the flowchart of FIG. 9 is that the data analysis section 442 outputs the pulse determination threshold determined by the first data analysis processing to the D-A converter 49 instead of the threshold processing unit 43. Herein, only the difference is described.

Upon receiving the pulse determination threshold determined by the data analysis section 442, the D-A converter 49 converts the pulse determination threshold from digital data to analogue pulse determination threshold. The D-A converter 49 outputs the analogue pulse determination threshold to the comparator 48.

The comparator 48 compares the analogue voltage signal inputted from the photomultiplier tube 3 with the analogue pulse determination threshold. When the analogue voltage signal is larger than the analogue pulse determination threshold, the comparator 48 outputs the count instruction signal to the counter 50. Upon receiving the count instruction signal, the counter 50 counts up the count value and outputs the count value to the PC 5. The PC 5 calculates the intensity of light or the number of pulses inputted into the photomultiplier tube 3 based on the count value.

As described above, in Embodiment 4, the data processing section 441 detects pulses from the digital voltage signal corresponding to the amount of light which is converted by the amplifier 41 and A-D converter 42 and calculates the crest value as the maximum voltage value of each detected pulse, and stores the occurrence frequency of each crest value in the frequency count storage area 451. The data analysis section 442 compares the previously determined frequency lower limit with the number of occurrences of each crest value which is stored in the frequency count storage area 451 in association with the crest value in ascending order of the crest values. As the result of the comparison, the first crest value whose number of occurrences is equal to or smaller than the frequency lower limit TH1 is set as the pulse determination threshold. The D-A converter 49 converts the pulse determination threshold to an analogue signal, and the number of times when the analogue voltage signal inputted from the photomultiplier tube 3 is equal to or larger than the pulse determination threshold of the analogue signal converted by the A-D converter 42 and is outputted to the PC 5.

Accordingly, the light signal detecting circuit 4a using the pulse count method also can discriminate the signal component of a very small amount of light from the signal component of noise due to dark current with the simple operation of setting the frequency lower limit TH1, thus increasing the S/N (signal-noise ratio).

In the description of Embodiment 4, the light amount detecting device includes the single photomultiplier 3. However, the light amount detecting device may include a plurality of the photomultipliers 3. In this case, the light signal detecting circuit 4a needs to include the same numbers of comparators and counters as the number of the photomultiplier tubes 3.

FIG. 17 is a block diagram illustrating the configuration of a light amount detecting device including two photomultiplier tubes. As illustrated in FIG. 17, the light amount detecting device includes plural (two in this case) photomultiplier tubes 3-1 and 3-2 detecting fluorescence from the sample 2. The light signal detecting circuit 4a includes the same numbers of (two in this case) comparators 48-1 and 48-2 and counters 50-1 and 50-2 as the number of photomultiplier tubes 3-1 and 3-2.

The photomultiplier tubes 3-1 and 3-2 are located at different positions and individually detect fluorescence from the sample 2. The photomultiplier tube 3-1 outputs analogue voltage signal as electric signal corresponding to the detected fluorescence to the amplifier 41 and comparator 48-1. The photomultiplier tube 3-2 outputs analogue voltage signal to the comparator 48-2.

In a similar manner to the comparator 48 illustrated in FIG. 16 above, the comparators 48-1 and 48-2 compare the analogue voltage signals inputted from the photomultiplier tubes 3-1 and 3-2 with the analogue pulse determination threshold inputted from the D-A converter, respectively. (Only) when the analogue signal is not smaller than the analogue pulse determination threshold as the result of the comparison, the comparators 48-1 and 48-2 each output a pulse to instruct to count up waveform shaping operations (count instruction signal) to the counters 50-1 and 50-2, respectively. When receiving the count instruction signals, each of the counters 50-1 and 50-2 counts up the count value and outputs the same to the PC 5.

As described above, the pulse determination threshold can be determined by the output from the one photomultiplier tube 3-1 even when the amount of light of the sample 2 is detected by the plural photomultiplier tubes 3-1 and 3-2. Accordingly, the circuit size of the light signal detecting circuit 4a can be reduced.

Embodiment 5

In the description of Embodiments 1 to 4 above, the light signal detecting circuit is applied to the light amount detecting devices. In the description of Embodiment 5, the light signal detecting circuit is applied to a scanning electron microscope as a kind of charged-particle beam devices.

FIG. 18 is a diagram illustrating the configuration of the scanning electron microscope including a light signal detecting circuit of the present invention. As illustrated in FIG. 18, the scanning electron microscope including the light signal detecting circuit of the present invention includes an electron source 601, an extraction electrode 602, an acceleration electrode 603, a first focusing electrode 605, a diaphragm 606, a second focusing electrode 607, an electron beam operation deflector 608, an ExB deflector 612, an objective lens 609, a sample stage 611, a secondary electron detector 614, a pre-amplifier 615, a high-voltage controller 620, a focusing lens controller 622, a deflection controller 623, a detection controller 624, an objective lens controller 625, a stage controller 626, and a computer 630.

The high-voltage controller 620 controls the electron source 601, extraction electrode 602, and acceleration electrode 603. The focusing lens controller 622 controls the first focusing electrode 605 and second focusing electrode 607. The deflection controller 623 controls the electron beam operation defector 608. The objective lens controller 625 controls the objective lens 609. The stage controller 626 controls the sample stage 611.

The detection controller 624 performs light detection from the signal which is detected by the secondary electron detector 614 and amplified by the pre-amplifier 615. The detecting controller 624 includes any one of the light signal detecting circuits of Embodiments 1 to 4 described above. The computer 630 displays an image of the surface profile of a sample 610 examined based on the signal detected by the detection controller 624.

Next, the operation of the scanning electron microscope of Embodiment 5 is described. Electrons emitted from the electron source 601 are accelerated by the extraction electrode 602 and acceleration electrode 603. The accelerated electrons 604 are narrowed through the first focusing electrode 605, diaphragm 606, and second focusing electrode 607. After transmitted through the ExB deflector 612, the electrons 604 are converged by the lens effect of the objective lens 609 and are caused to one-dimensionally or two-dimensionally scan on the examined sample 610 which is placed on the sample stage 611.

The secondary electrons 613 generated from the examined sample 610 reach the secondary electron detector 614 through the ExB deflector 612. The secondary electron detector 614 outputs voltage signal corresponding to the received secondary electrons 614 to the pre-amplifier 615. The pre-amplifier 615 amplifies the voltage signal and outputs the same to the detection controller 624.

The detection controller 624 is any one of the light signal detecting circuits of Embodiments 1 to 4 described above. By any one of the operations of Embodiments 1 to 4, the detection controller 624 determines the pulse determination threshold and outputs the output pulses or the count value of the number of output pulses to the computer 630 based on the determined pulse determination threshold.

The computer 630 displays an image of the surface profile of the examined sample 610 through the display means such as a monitor based on the output pulses or the count value of the number of output pulses inputted from the detection controller 624.

As described above, in Embodiment 5, the detection controller 624 is anyone of the light signal detecting circuits of Embodiments 1 to 4. Accordingly, the detection controller 624 can discriminate the signal component of a very small amount of light from the signal component of noise due to dark current with a simple operation including setting the frequency lower limit TH1 and can discriminate the signal component of a very small amount of light from the signal component of noise due to dark current in response to the changes thereof. Accordingly, the scanning electron microscope including the detection controller 624 can provide higher S/N (signal-noise ratio) of light signal detection.

Embodiment 5 is described by taking the scanning electron microscope as an example of the charged particle beam device. However, the present invention is not limited thereto. Any one of the light signal detecting circuits of Embodiments 1 to 4 may be used for detection by the device detecting and analyzing light from measurement objects, such as ion microscopes, for example.

EXPLANATION OF THE REFERENCE NUMERALS

1 . . . LIGHT SOURCE
2 . . . SAMPLE
3 . . . PHOTOMULTIPLIER TUBE (LIGHT DETECTING MEANS)
4 . . . LIGHT SIGNAL DETECTING CIRCUIT
5 . . . PERSONAL COMPUTER (CONTROLLING MEANS)
41 . . . AMPLIFIER (AMPLIFYING MEANS)
42 . . . A-D CONVERTER (ANALOGUE-TO-DIGITAL CONVERTING MEANS)
43 . . . THRESHOLD PROCESSING UNIT (THRESHOLD PROCESSING MEANS)
44 . . . THRESHOLD DETERMINATION UNIT (THRESHOLD DETERMINATION MEANS)
46, 46a . . . GAIN CONTROLLER (GAIN CONTROLLING MEANS)
47 . . . PULSE MEASUREMENT CONTROLLER (PULSE MEASUREMENT CONTROLLING MEANS)
48 . . . COMPARATOR (COMPARING MEANS)
49 . . . D-A CONVERTER (DIGITAL-TO-ANALOGUE CONVERTING MEANS)
50 . . . COUNTER (COUNTING MEANS)
441 . . . DATA PROCESSING SECTION (DATA PROCESSING MEANS)
442, 442a . . . DATA ANALYSIS SECTION (DATA ANALYZING MEANS)
451 . . . FREQUENCY COUNT STORAGE AREA (FREQUENCY COUNT STORING MEANS)
452 . . . PULSE NUMBER STORAGE AREA (PULSE NUMBER STORING MEANS)

The invention claimed is:
1. A light signal detecting circuit, comprising:
amplifying means for amplifying an analogue detection signal corresponding to an amount of light detected by light detecting means;
analogue-to-digital converting means for converting the analogue detection signal amplified by the amplifying means to a digital detection signal;
threshold determination means for: repeating a process to detect a pulse from the digital detection signal obtained by the analogue-to-digital converting means and detect energy of the detected pulse; calculating an occurrence frequency of the pulses of each value of the energy; and determining a pulse determination threshold based on the calculated occurrence frequency of the pulses of each value of the energy; and
threshold processing means for outputting, as a detection signal, the digital detection signal including the pulses of the values of the energy not lower than the pulse determination threshold determined by the threshold determination means.

2. The light signal detecting circuit according to claim 1, further comprising:
frequency count storing means for storing the occurrence frequency of the detected pulses of each value of the energy in association with the value of the energy, wherein
the threshold determination means includes:
data processing means for performing a process to store the occurrence frequency of the pulses of each value of the energy in the frequency count storing means; and
data analyzing means for sequentially comparing a previously determined frequency lower limit with the occurrence frequency of the pulses of each value of the energy, which is stored in the frequency count storing means, in ascending order of the value of the energy and for determining a pulse determination threshold to be the first value of the energy whose occurrence frequency of the pulses is equal to or lower than the frequency lower limit as the result of the comparison.

3. The light signal detecting circuit according to claim 1, further comprising:
frequency count storing means for storing the occurrence frequency of the detected pulses of each value of the energy in association with the value of the energy, wherein
the threshold determination means includes:
data processing means for performing a process to store the occurrence frequency of the pulses of each value of the energy in the frequency count storing means; and
data analyzing means for sequentially comparing the occurrence frequency of the detected pulses of each value of the energy, which is stored in the frequency count storing means, in ascending order of the values of the energy to calculate the smallest occurrence frequency of the detected pulses and for determining a pulse determination threshold to be a value of the energy whose occurrence frequency of the pulses is equal to the calculated smallest occurrence frequency.

4. A light signal detecting circuit, comprising:
amplifying means for amplifying an analogue detection signal corresponding to an amount of light detected by light detecting means;
analogue-to-digital converting means for converting the analogue detection signal amplified by the amplifying means to a digital detection signal;
threshold determination means for: repeating a process to detect a pulse from the digital detection signal obtained by the analogue-to-digital converting means and detect energy of the detected pulse; calculating an occurrence frequency of the pulses of each value of the energy; and determining a pulse determination threshold based on the calculated occurrence frequency of the pulses of each value of the energy;
digital-to-analogue converting means for converting the pulse determination threshold determined by the threshold determination means from the digital signal to an analogue signal;
comparing means for determining whether the analogue detection signal corresponding to the detected amount of light is not smaller than the pulse determination threshold of the analogue signal converted by the digital-to-analogue converting means; and
counting means for counting and outputting the number of times when it is determined by the comparing means that the analogue detection signal corresponding to the detected amount of light is not smaller than the pulse determination threshold of the analogue signal obtained by the digital-to-analogue converting means.

5. The light signal detecting circuit according to claim 4, further comprising:
frequency count storing means for storing the occurrence frequency of the detected pulses of each value of the energy in association with the value of the energy, wherein
the threshold determination means includes:
data processing means for performing a process to store the occurrence frequency of the pulses of each value of the energy in the frequency count storing means; and
data analyzing means for sequentially comparing a previously determined frequency lower limit with the occurrence frequency of the pulses of each value of the energy, which is stored in the frequency count storing means, in ascending order of the value of the energy and for determining a pulse determination threshold to be the first value of the energy whose occurrence frequency of the pulses is equal to or lower than the frequency lower limit as the result of the comparison.

6. The light signal detecting circuit according to claim 4, further comprising:
frequency count storing means for storing the occurrence frequency of the detected pulses of each value of the energy in association with the value of energy, wherein
the threshold determination means includes:
data processing means for performing a process to store the occurrence frequency of the pulses of each value of the energy in the frequency count storing means; and
data analyzing means for sequentially comparing the occurrence frequency of the detected pulses of each value of the energy, which is stored in the frequency count storing means, in ascending order of the values of the energy to calculate the smallest occurrence frequency of the detected pulses and for determining a pulse determination threshold to be a value of the energy whose occurrence frequency of the pulses is equal to the calculated smallest occurrence frequency.

7. A charged particle beam device, comprising the light signal detecting circuit according to claim 1.

* * * * *